US012643864B2

(12) United States Patent
Qian

(10) Patent No.: US 12,643,864 B2
(45) Date of Patent: Jun. 2, 2026

(54) ETHOXY/PROPOXY MODIFIED PYRAZOLINE ORGANIC MATTER, APPLICATION THEREOF, PHOTOCURABLE COMPOSITION, AND PHOTORESIST

(71) Applicants: CHANGZHOU TRONLY NEW ELECTRONIC MATERIALS CO., LTD., Jiangsu (CN); CHANGZHOU TRONLY ADVANCED ELECTRONIC MATERIALS CO., LTD., Jiangsu (CN)

(72) Inventor: Xiaochun Qian, Jiangsu (CN)

(73) Assignees: Changzhou Tronly New Electronic Materials Co., Ltd., Jiangsu (CN); Changzhou Tronly Advanced Electronic Materials Co., Ltd., Jiangsu (CN)

( * ) Notice: Subject to any disclaimer, the term of this patent is extended or adjusted under 35 U.S.C. 154(b) by 735 days.

(21) Appl. No.: 17/996,773

(22) PCT Filed: Mar. 16, 2021

(86) PCT No.: PCT/CN2021/081187
§ 371 (c)(1),
(2) Date: Oct. 20, 2022

(87) PCT Pub. No.: WO2021/213087
PCT Pub. Date: Oct. 28, 2021

(65) Prior Publication Data

US 2023/0167066 A1 Jun. 1, 2023

(30) Foreign Application Priority Data

Apr. 22, 2020 (CN) ........................ 202010323287.7

(51) Int. Cl.

| | |
|---|---|
| ***C07D 231/06*** | (2006.01) |
| ***G03F 7/004*** | (2006.01) |
| ***G03F 7/031*** | (2006.01) |

(52) U.S. Cl.
CPC ......... *C07D 231/06* (2013.01); *G03F 7/0045* (2013.01); *G03F 7/031* (2013.01)

(58) Field of Classification Search
CPC ...... C07D 231/06; G03F 7/0045; G03F 7/031
See application file for complete search history.

(56) References Cited

U.S. PATENT DOCUMENTS 5,750,590 A 5/1998 Schaefer et al.

FOREIGN PATENT DOCUMENTS

| | | | |
|---|---|---|---|
| CN | 1451712 | A | 10/2003 |
| CN | 1515557 | A | 7/2004 |
| CN | 104781730 | A | 7/2015 |
| CN | 104876807 | A | 9/2015 |
| CN | 104892512 | A | 9/2015 |
| CN | 104892513 | A | 9/2015 |
| CN | 105085718 | A | 11/2015 |
| DE | 3839696 | A1 | 6/1989 |
| GB | 2216674 | | 10/1989 |
| JP | 2008116751 | A | 5/2008 |
| JP | 2009058537 | A | 3/2009 |
| JP | 2009229655 | A | 10/2009 |
| JP | 2012208528 | A | 10/2012 |
| JP | 2012215787 | A | 11/2012 |
| JP | 2018524285 | A | 8/2018 |

(Continued)

OTHER PUBLICATIONS

STN Registry entry for CAS RN 2454504-93-7, Accessed from STNext, Entry date Aug. 10, 2020, Accessed May 17, 2025.*
STN Registry entry for CAS RN 443668-26-6, Accessed from STNext, Entry date Aug. 12, 2002, Accessed May 17, 2025.*
Chinese Office Action received in Chinese Application No. 202010323287.7, dated Dec. 27, 2022, in 6 pages.
Supplementary European Search Report received in European Application No. 21793446.2, dated Mar. 25, 2024, in 8 pages.
Jin et al., "Fluorescence modulation in azobenzene-substituted triphenyl pyrazoline derivative", Optical Materials, vol. 26, Issue 1, 2004, pp. 85-88.
Wei et al., "Synthesis of novel light-emitting calix[4]arene derivatives and their luminescent properties", Optical Materials, vol. 29, Issue 8, 2007, pp. 936-940.

(Continued)

*Primary Examiner* — Alicia L Otton
(74) *Attorney, Agent, or Firm* — Knobbe, Martens, Olson & Bear, LLP

(57) ABSTRACT

An ethoxy/propoxy modified pyrazoline organic matter, an application thereof, a photocurable composition, and a photoresist. The introduction of $—CH_2—CH_2—O(EO)$ and/or $—CH(CH_3)—CH_2—O(PO)$ enables an EO/PO modified pyrazoline organic matter to have excellent compatibility with other components in a photocuring system, and the organic matter is solid, and is easy to add and use. In addition, the ethoxy/propoxy modified pyrazoline organic matter has an absorption band of 360-400 nm, and is thus particularly suitable for use as a sensitizer in the photocuring system (such as a system containing a bisimidazole photoinitiator), thereby greatly improving the sensitivity of the photocuring system. On this basis, the EO/PO modified pyrazoline organic matter has high sensitivity enhancement, features low usage, is solid, and is easy to add and use.

(I)

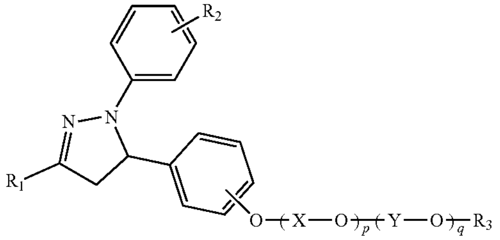

12 Claims, No Drawings

(56) References Cited

FOREIGN PATENT DOCUMENTS

| | | | |
|---|---|---|---|
| TW | 201627758 | A | 8/2016 |
| WO | WO 2009060235 | A1 | 5/2009 |
| WO | WO 2016184429 | A1 | 11/2016 |
| WO | WO 2019147011 | A1 | 8/2019 |

OTHER PUBLICATIONS

Yusuf et al., "New Bispyrazoline Derivatives Built Around Aliphatic Chains: Synthesis, Characterization and Antimicrobial Studies", Journal of Chemical Sciences, vol. 125, No. 1, Jan. 2013, pp. 117-127.

Notice of Reasons for Refusal issued in Japanese Application No. 2022-563920, dated Oct. 24, 2023.

Registry (STN) [online], search on Oct. 17, 2023, CAS Registration No. 443668-26-6, Aug. 12, 2002.

Registry (STN) [online], search on Oct. 17, 2023, CAS Registration No. 443297-77-6, Aug. 9, 2002.

Registry (STN) [online], search on Oct. 17, 2023, CAS Registration No. 443295-94-1, Aug. 9, 2002.

Registry (STN) [online], search on Oct. 17, 2023, CAS Registration No. 443298-10-0, Aug. 9, 2002.

Registry (STN) [online], search on Oct. 17, 2023, CAS Registration No. 443636-47-3, Aug. 12, 2002.

Registry (STN) [online], search on Oct. 17, 2023, CAS Registration No. 443637-99-8, Aug. 12, 2002.

Registry (STN) [online], search on Oct. 17, 2023, CAS Registration No. 443667-06-9, Aug. 12, 2002.

Registry (STN) [online], search on Oct. 17, 2023, CAS Registration No. 444117-71-9, Aug. 16, 2002.

Registry (STN) [online], search on Oct. 17, 2023, CAS Registration No. 444058-43-9, Aug. 16, 2002.

Registry (STN) [online], search on Oct. 17, 2023, CAS Registration No. 443667-34-3, Aug. 12, 2002.

Office Action issued in Taiwanese Application No. 110113585, issued on Mar. 15, 2022.

International Search Report issued in International Application No. PCT/CN2021/081187, mailed on Jun. 17, 2021.

Xiheng, Dai, "Pyrazolone and Synthesis thereof", Shenyang Chemical Industry Research Institute, Dec. 31, 1977, in 10 pages.

* cited by examiner

ETHOXY/PROPOXY MODIFIED PYRAZOLINE ORGANIC MATTER, APPLICATION THEREOF, PHOTOCURABLE COMPOSITION, AND PHOTORESIST

TECHNICAL FIELD

The invention relates to the field of photocuring, and specifically to ethoxy/propoxy modified pyrazoline organic compounds, applications thereof, photocurable compositions, and photoresists.

BACKGROUND

UV-curing technology has been widely used due to its advantages such as fast curing speed, low environmental pollution, etc., in which the photoinitiator plays a decisive role in the curing efficiency of the whole curing system. In practical use, some photoinitiators cannot initiate the polymerization well due to the limitation of absorption wavelength, and often need to be used in conjunction with a sensitizer to improve the initiation efficiency. The sensitizer can continuously transfer the absorbed energy to the photoinitiator, which is equivalent to a catalyst of a photochemical reaction. However, the application of the sensitizer is restricted by many factors, such as solubility, matching to absorption wavelength, etc. At this stage, finding a sensitizer that matches the absorption wavelength of the photoinitiator and has good intermiscibility has always been a research and development hotspot in this field.

Pyrazoline compounds are a very important class of sensitizers and have been widely used. However, when these existing pyrazoline compounds are used as sensitizers, there are more or less disadvantages such as unsatisfactory solubility, poor sensitivity enhancement effect, etc.

In dry film development stage, unexposed portion is usually washed away with an alkaline aqueous solution, and pyrazoline compounds will be precipitated and adsorbed on the surface of a circuit board at this time, due to its extremely low solubility. This will not only affect the use of the dry film, but also reduce the precision of the product. Thus, it is necessary to subsequently add a cleaning process of the surface of the circuit board, resulting in a cumbersome process and a great increase in cost.

The existing literature provides a pyrazoline macromolecular sensitizer, which solves the problems involving the solubility, formulation compatibility, etc. However, it is found in practical applications that, there are problems such as large addition amount, insufficient sensitivity enhancement, and inconvenient use due to large viscosity. Therefore, there is a need for further optimization.

SUMMARY

A main object of the invention is to provide an ethoxy/propoxy modified pyrazoline organic compound, an application thereof, a photocurable composition, and a photoresist, so as to solve the problems of the existing pyrazoline macromolecular sensitizers, such as large addition amount, insufficient sensitivity enhancement, and inconvenient use due to large viscosity.

In order to achieve the above object, according to one aspect of the invention, there is provided an ethoxy/propoxy modified pyrazoline organic compound having a structure represented by Formula (I):

Formula (I)

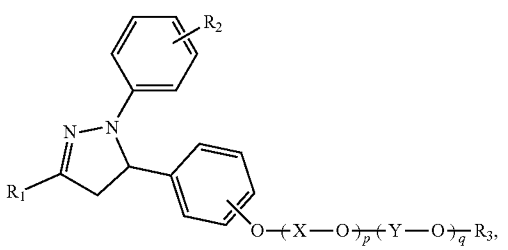

wherein X and Y each independently represent —$CH_2$—$CH_2$— or —$CH(CH_3)$—$CH_2$—; p and q each independently represent an integer from 0 to 9, and both are not 0 at the same time; $R_1$ represents a substituent group having a conjugated structure with the pyrazole ring; $R_2$ represents hydrogen, $C_1$ to $C_{10}$ linear or branched alkyl, or $C_4$ to $C_{10}$ alkylcycloalkyl or cycloalkylalkyl; $R_3$ represents hydrogen, $C_1$ to $C_{20}$ hydrocarbon group, or $C_6$ to $C_{20}$ arylalkyl.

Further, p+q≤9; preferably, p+q≤6.

Further, $R_1$ is selected from phenyl, naphthyl, pyrrolyl, imidazolyl, carbazolyl, indolyl, $C_2$ to $C_{10}$ alkenyl, or $C_4$ to $C_8$ cyclodienyl, or the hydrogen atom(s) therein may be each independently substituted by: $C_1$ to $C_{10}$ linear or branched alkyl, $C_4$ to $C_{10}$ alkylcycloalkyl or cycloalkylalkyl, $C_3$ to $C_{10}$ cycloalkyl, $C_6$ to $C_{15}$ aryl, $C_6$ to $C_{12}$ alkylaryl, $C_6$ to $C_{12}$ arylalkyl, or $C_2$ to $C_{20}$ heteroaryl; $R_2$ is selected from hydrogen, or $C_1$ to $C_6$ linear or branched alkyl; $R_3$ is selected from hydrogen, $C_1$-$C_6$ linear or branched alkyl, or benzyl.

Further, $R_1$ is selected from phenyl, naphthyl, pyrrolyl, imidazolyl, carbazolyl, indolyl, $C_2$ to $C_6$ alkenyl, $C_4$ to $C_6$ cyclodienyl, phenyl substituted by $C_1$ to $C_5$ alkyl, phenyl substituted by $C_3$ to $C_6$ cycloalkyl, alkenyl substituted by $C_6$ to $C_{10}$ aryl, alkenyl substituted by $C_6$ to $C_{10}$ alkylaryl, or alkenyl substituted by $C_6$ to $C_{10}$ arylalkyl.

Further, $R_1$ is selected from:

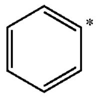 , 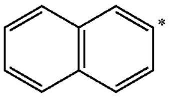 , 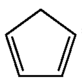 , 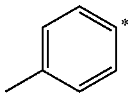 ,

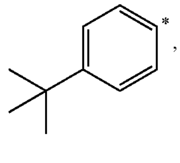 , 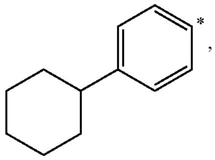 ,

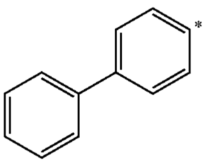 , 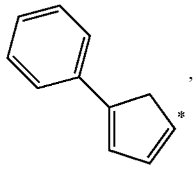 ,

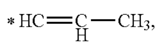 , 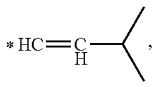 , 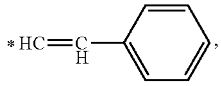 ,

-continued
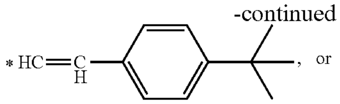
, or
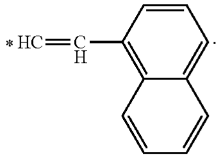
.
Further, $R_2$ is selected from hydrogen, methyl, ethyl, propyl, isopropyl, butyl, tert-butyl, or $CH_3C(CH_2CH_3)_2$—.
Further, the ethoxy/propoxy modified pyrazoline organic compound is selected from one or more of the following organic compounds:
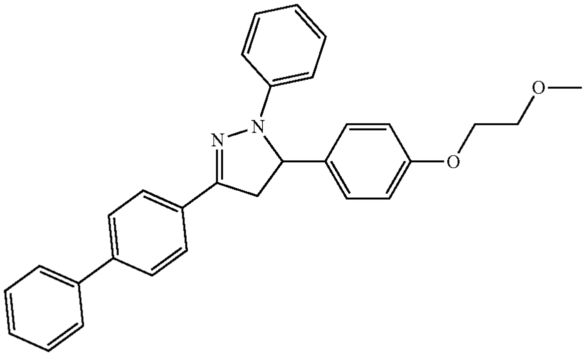
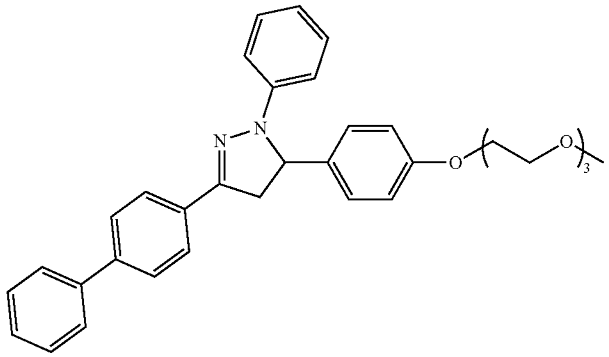
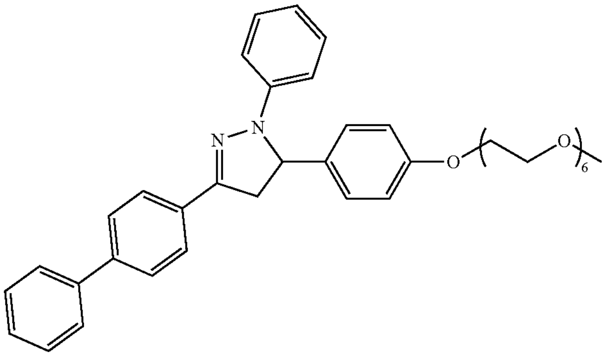
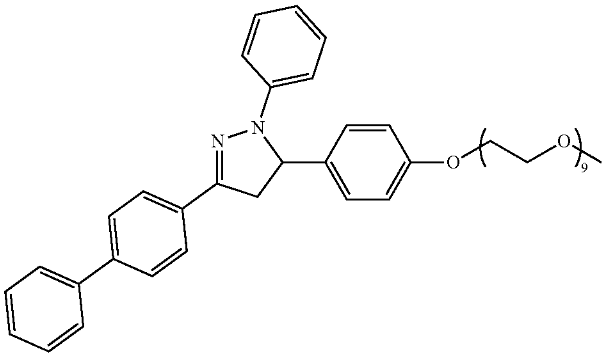
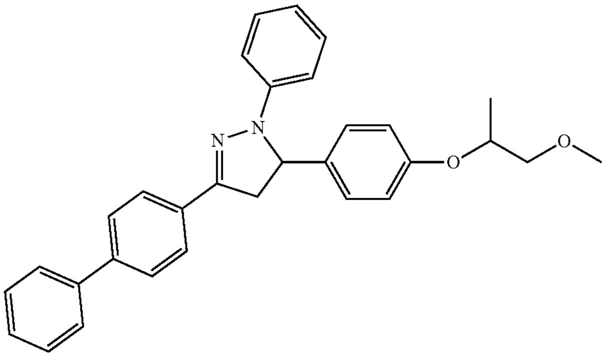

-continued
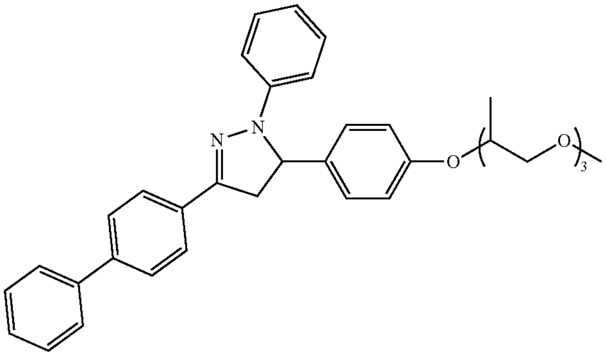
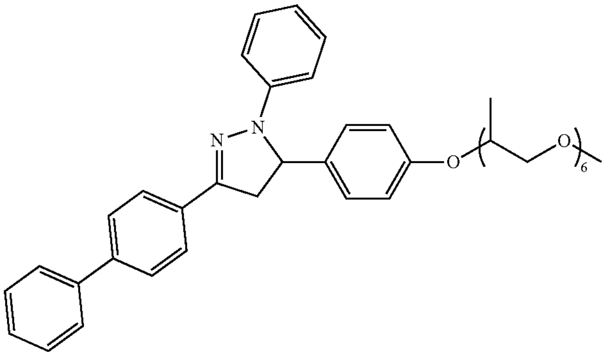
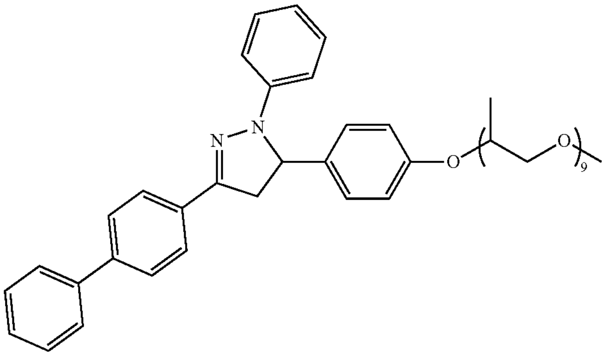
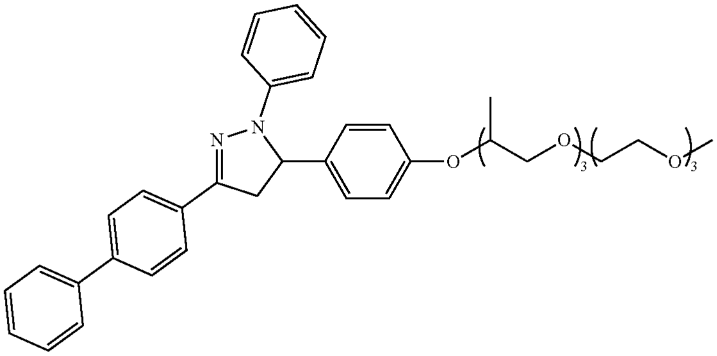

-continued
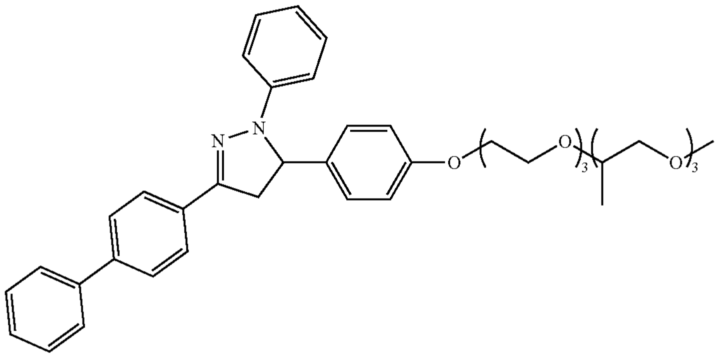
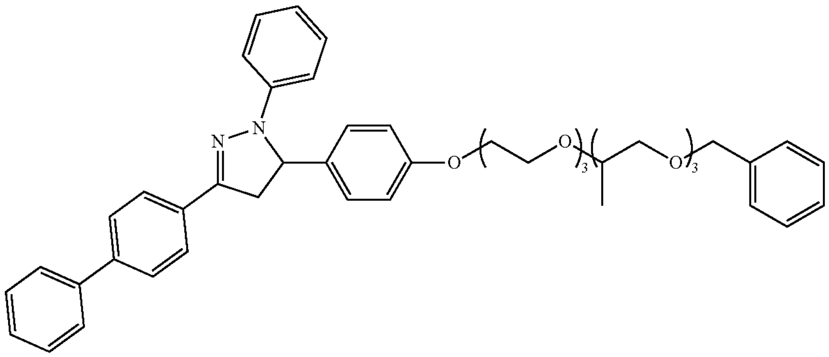
lp;3p
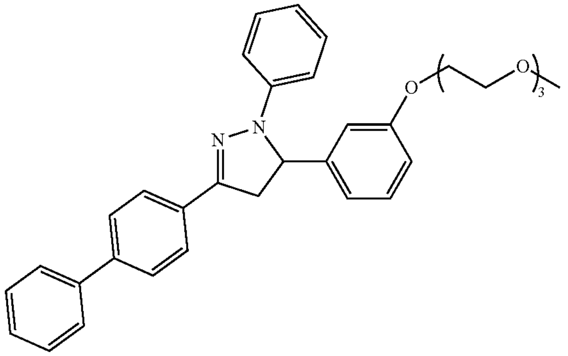
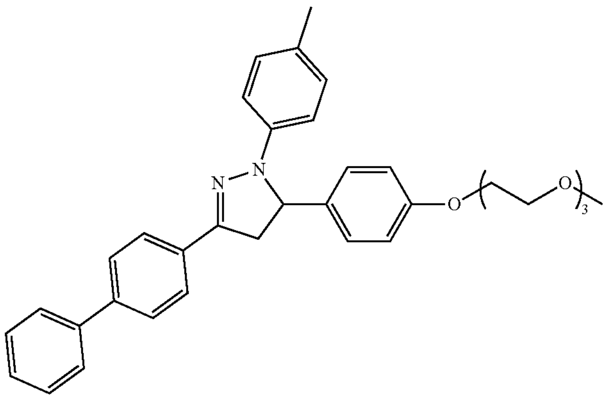

-continued

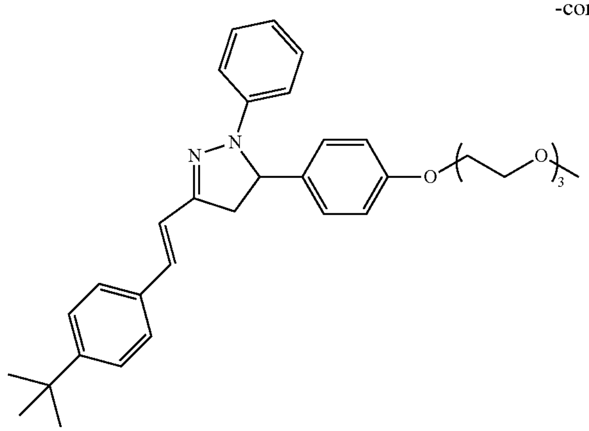

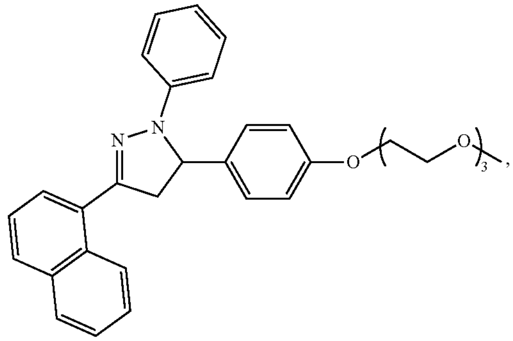

,

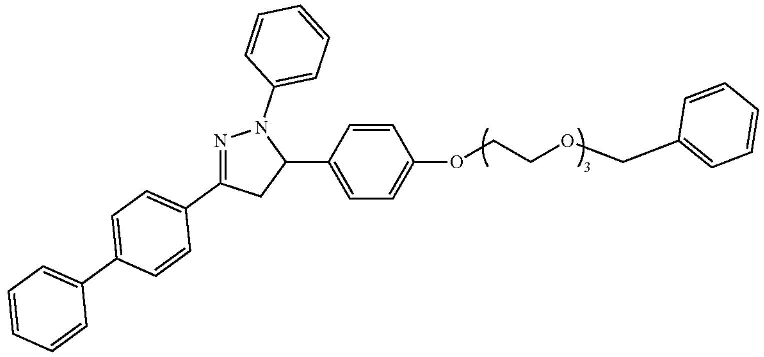

.

Another aspect of the invention further provides a photocurable composition, characterized in comprising: (A) an alkali-soluble polymer, (B) a compound having an ethylenically unsaturated double bond, (C) a first sensitizer, (D) a photoinitiator and/or a second sensitizer, and (E) other optional auxiliary agent(s), wherein the first sensitizer includes the above ethoxy/propoxy modified pyrazoline organic compound, and the second sensitizer is of a different kind from the first sensitizer.

Further, the alkali-soluble polymer is selected from one or more of the group consisting of (meth)acrylic polymers, styrenic polymers, epoxy polymers, aliphatic polyurethane (meth)acrylate polymers, aromatic polyurethane (meth) acrylate polymers, amide resins, amide epoxy resins, alkyd resins, and phenolic resins.

Further, the compound having an ethylenically unsaturated double bond is selected from one or more of the group consisting of compounds obtained by reacting α,β-unsaturated carboxylic acids with polyols, bisphenol A-based (meth)acrylate compounds, compounds obtained by reacting α,β-unsaturated carboxylic acids with glycidyl-containing compounds, (meth)acrylate compounds having a urethane bond in the molecule, nonylphenoxypolyethyleneoxyacrylates, γ-chloro-β-hydroxypropyl-β'-(meth)acryloyloxyethyl-phthalates, β-hydroxyethyl-β'-(meth)acryloyloxyethyl-phthalates, β-hydroxypropyl-β'-(meth)acryloyloxyethyl-phthalates, benzene dicarboxylic acid compounds, and alkyl (meth)acrylates.

Further, the auxiliary agent is selected from one or more of the group consisting of hydrogen donors, dyes, pigments, light chromogenic reagents, fillers, plasticizers, stabilizers, coating aids, and stripping promoters.

Yet another aspect of the invention further provides use of the ethoxy/propoxy modified pyrazoline organic compound in the field of photocuring.

Yet another aspect of the invention further provides a photoresist comprising the above photocurable composition.

By using the technical solution of the invention, due to the introduction of $-CH_2-CH_2-O(EO)$ and/or $-CH(CH_3)-CH_2-O(PO)$, the above EO/PO modified pyrazoline organic compound has excellent compatibility with other components in the photocuring system.

Moreover, it is solid and thus it is convenient to add and use. At the same time, the structure represented by Formula (I) has an absorption band of 360-400 nm and especially suitable for use as sensitizer in a photocuring system (such as a system containing bisimidazole photoinitiator), and can greatly improve the photosensitivity of the photocuring system. In view of this, the EO/PO modified pyrazoline organic compound with the above structure has high sensitivity enhancements and small usage amounts. Moreover, it is solid and thus it is convenient to add and use.

DETAILED DESCRIPTION OF THE PREFERRED EMBODIMENTS

It should be noted that, in the case of no conflict, the embodiments in the subject application as well as the features therein can be combined with each other. The invention will be described in detail below with reference to the embodiments.

The terms "sludge" and "developed waste" in the subject application refer to substances accumulated in the developer, which are insoluble in the developer and will re-deposit on the developed substrate, thereby reducing the efficiency of the developer.

As described in the background, the existing pyrazoline macromolecular sensitizers have the problems such as large addition amount, insufficient sensitivity enhancement, and inconvenient use due to large viscosity. In order to solve the above technical problems, the invention provides an ethoxy/propoxy modified pyrazoline organic compound having a structure represented by Formula (I):

Formula (I)

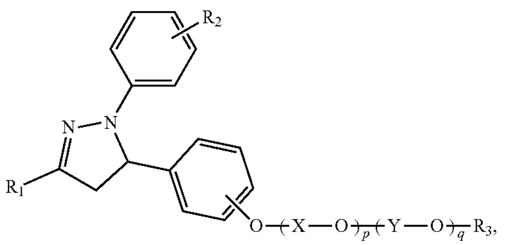

wherein X and Y each independently represent $-CH_2-CH_2-$ or $-CH(CH_3)-CH_2-$; p and q each independently represent an integer from 0 to 9, and both are not 0 at the same time; $R_1$ represents a substituent group having a conjugated structure with the pyrazole ring; $R_2$ represents hydrogen, $C_1$ to $C_{10}$ linear or branched alkyl, or $C_4$ to $C_{10}$ alkylcycloalkyl or cycloalkylalkyl; $R_3$ represents hydrogen, $C_1$ to $C_{20}$ hydrocarbon group, or $C_6$ to $C_{20}$ arylalkyl.

Due to the introduction of $-CH_2-CH_2-O$(EO) and/or $-CH(CH_3)-CH_2-O$(PO), the above EO/PO modified pyrazoline organic compound has excellent water solubility or water emulsibility. Moreover, it is solid and thus it is convenient to add and use. At the same time, the structure represented by Formula (I) has an absorption band of 360-400 nm and especially suitable for use as sensitizer in a photocuring system (such as a system containing bisimidazole photoinitiator), and can greatly improve the photosensitivity of the photocuring system. In view of this, the EO/PO modified pyrazoline organic compound with the above structure has high sensitivity enhancements, small usage amounts, and convenience to add and use.

In consideration of cost, production yield, and the like, in a preferred embodiment, p+q≤9; more preferably, p+q≤6.

In order to further improve the comprehensive performances of the EO/PO modified pyrazoline organic compound, in a preferred embodiment, $R_1$ is selected from phenyl, naphthyl, pyrrolyl, imidazolyl, carbazolyl, indolyl, $C_2$ to $C_{10}$ alkenyl, $C_4$ to $C_8$ cyclodienyl, or the hydrogen atom(s) therein may be each independently substituted by: $C_1$ to $C_{10}$ linear or branched alkyl, $C_4$ to $C_{10}$ alkylcycloalkyl or cycloalkylalkyl, $C_3$ to $C_{10}$ cycloalkyl, $C_6$ to $C_{15}$ aryl, $C_6$ to $C_{12}$ alkylaryl, $C_6$ to $C_{12}$ arylalkyl, or $C_2$ to $C_{20}$ heteroaryl; $R_2$ is selected from hydrogen, or $C_1$ to $C_6$ linear or branched alkyl; and $R_3$ is selected from hydrogen, $C_1$-$C_6$ linear or branched alkyl, or benzyl.

In order to further improve the conjugation between $R_1$ and the sensitizer represented by Formula (I) to improve its photosensitivity, preferably, $R_1$ is selected from phenyl, naphthyl, pyrrolyl, imidazolyl, carbazolyl, indolyl, $C_2$ to $C_6$ alkenyl, $C_4$ to $C_6$ cyclodienyl, phenyl substituted by $C_1$ to $C_5$ alkyl, phenyl substituted by $C_3$ to $C_6$ cycloalkyl, alkenyl substituted by $C_6$ to $C_{10}$ aryl, alkenyl substituted by $C_6$ to $C_{10}$ alkylaryl, or alkenyl substituted by $C_6$ to $C_{10}$ arylalkyl. In order to further reduce the synthesis difficulty of the EO/PO modified pyrazoline organic compound, more preferably, $R_1$ is selected from one of the following groups:

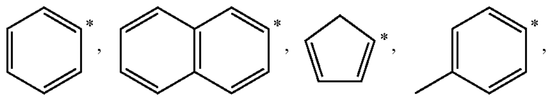

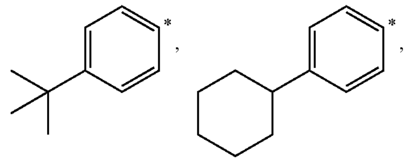

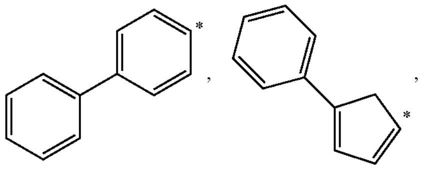

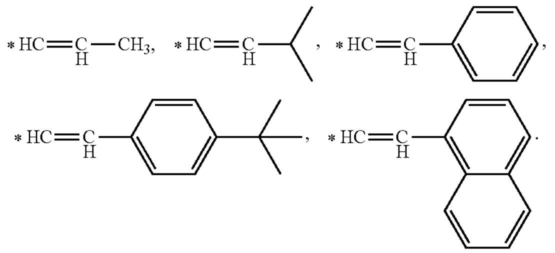

In order to reduce the synthesis difficulty and improve the water solubility or water emulsibility of the sensitizer, in a preferred embodiment, $R_2$ is selected from hydrogen, methyl, ethyl, propyl, isopropyl, butyl, tert-butyl, or $CH_3C(CH_2CH_3)_2-$.

In a preferred embodiment, the ethoxy/propoxy modified pyrazoline organic compound is selected from one or more of the following organic compounds:

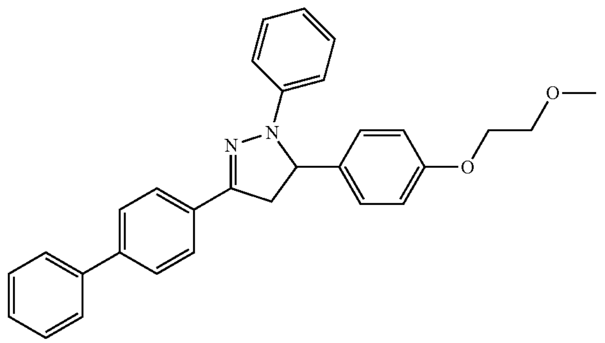
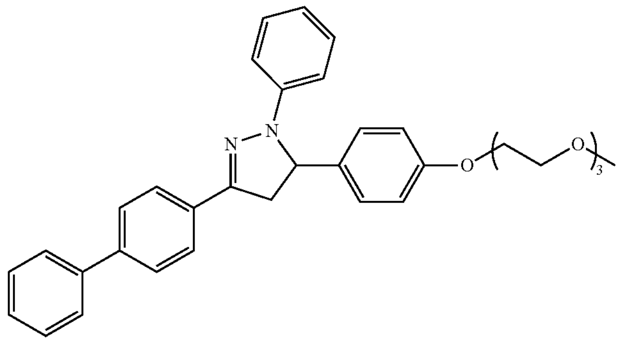
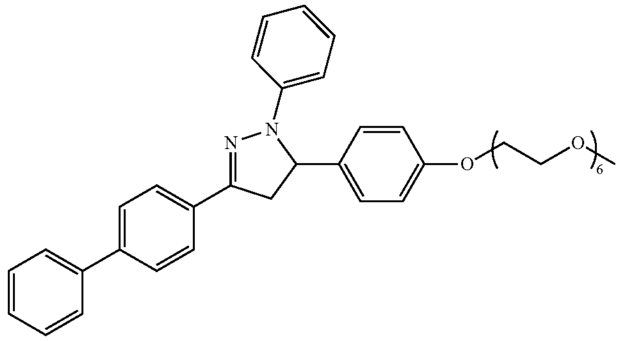
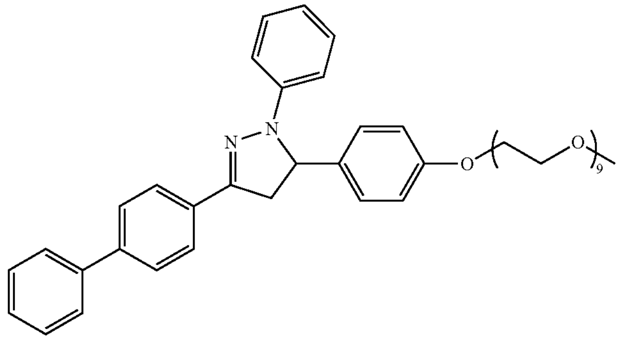
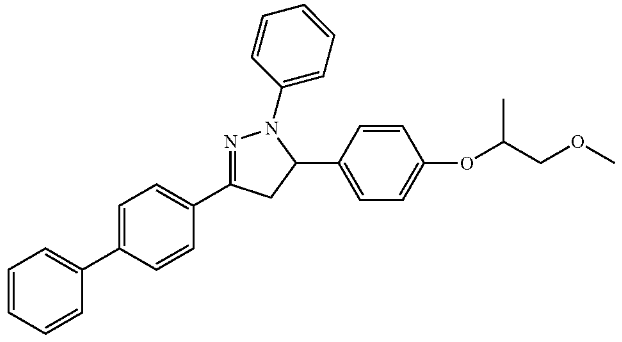

-continued
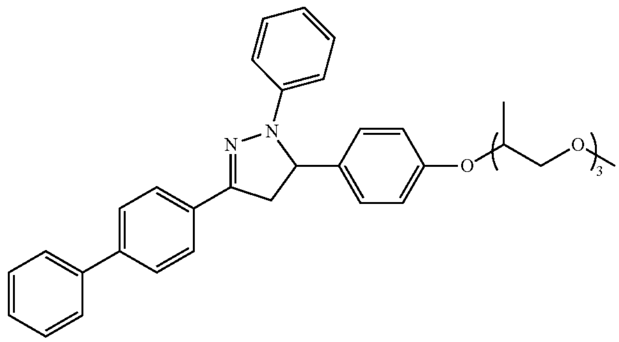
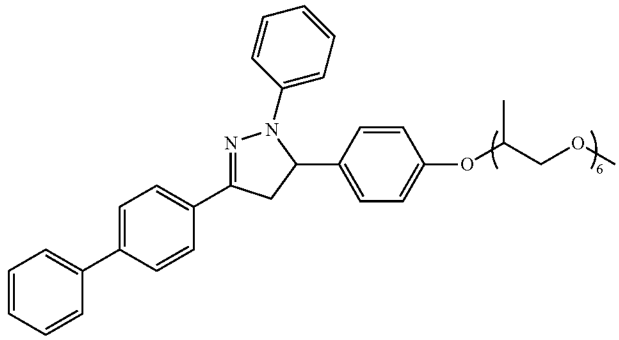
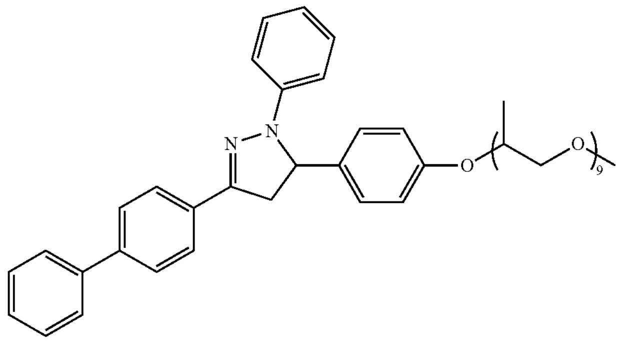
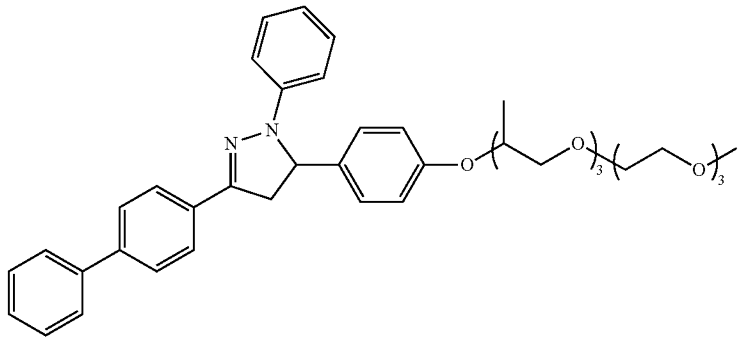
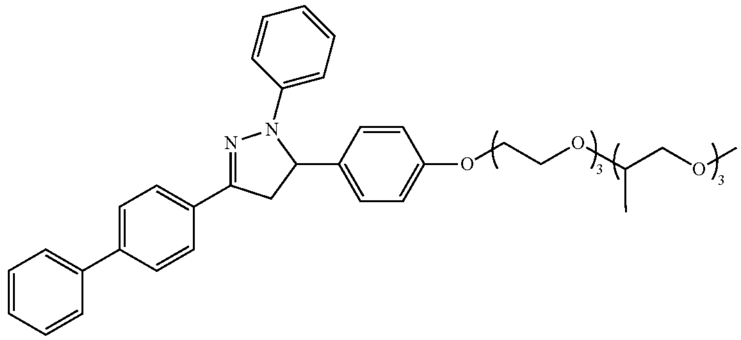

-continued

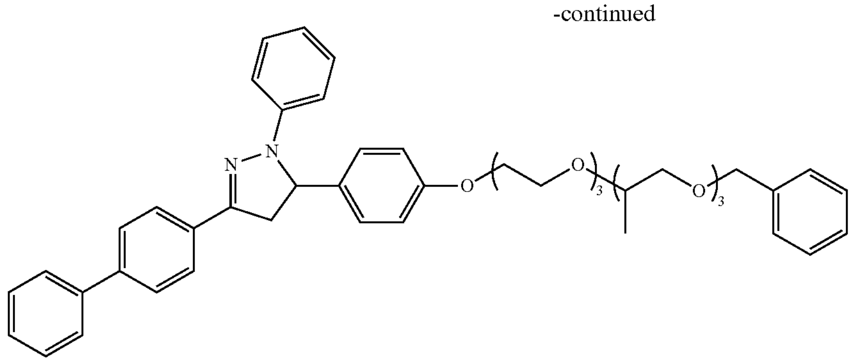

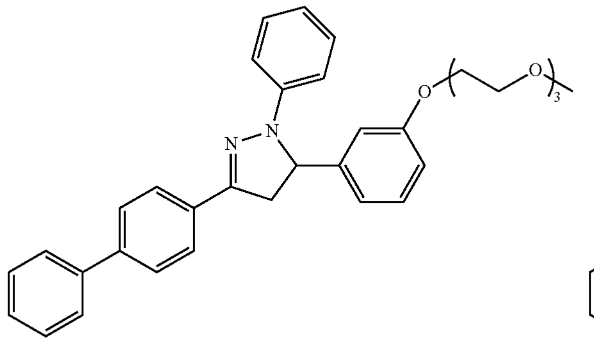

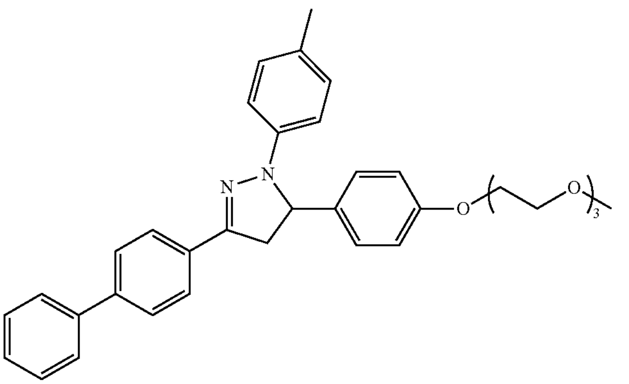

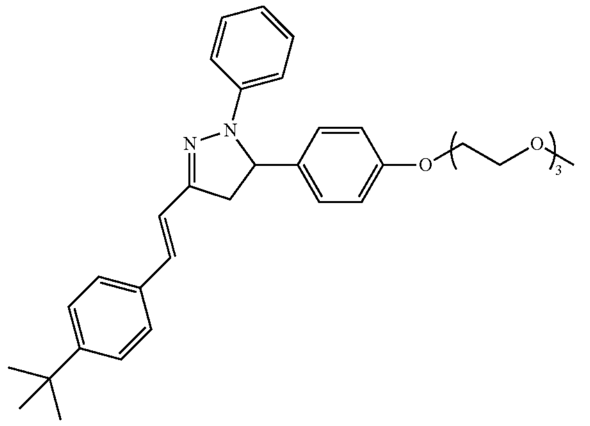

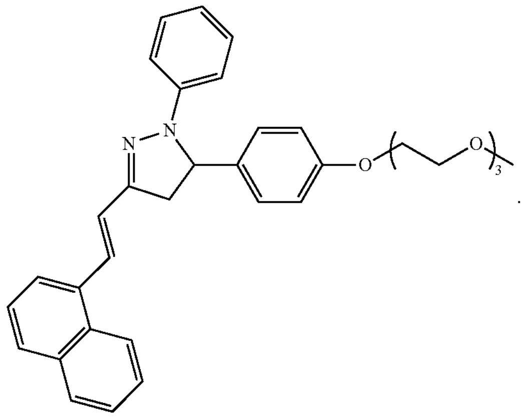

Compared with sensitizers of other structures, the above sensitizers have the advantages such as good photosensitivity, suitable viscosity during use, good adhesion, low synthesis difficulty, etc.

The invention also provides a method for preparing the EO/PO modified pyrazoline sensitizer represented by Formula (I), including the following steps:

(1) Reacting a raw material a and a raw material b in a solvent containing a catalyst to obtain an intermediate A;

(2) Reacting the intermediate A and a raw material c under the action of a strong base to obtain an intermediate B;

(3) Reacting the intermediate B under the action of an acid to obtain an intermediate C;

(4) Reacting the intermediate C and a raw material d in glacial acetic acid at 30-100° C. for 2-20 h to obtain an intermediate D;

(5) Reacting the raw material e and a raw material f in a solvent containing an acid-binding agent to obtain an intermediate E; and (6) Reacting the intermediate D and the intermediate E in a solvent containing an acid-binding agent to obtain a product F.

The reaction equations are as follows:

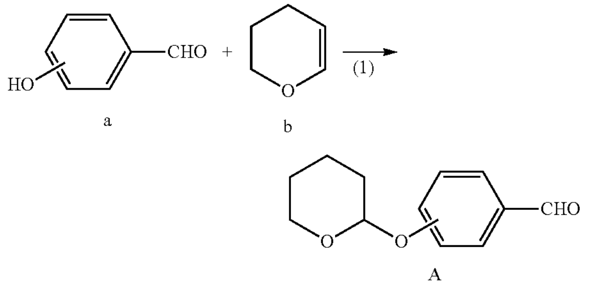

-continued

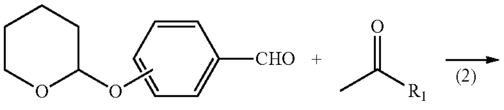

A c

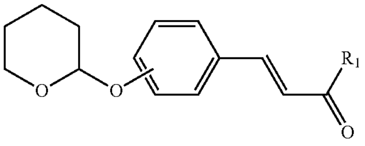

B

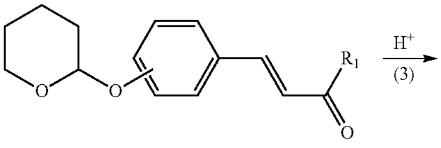

B

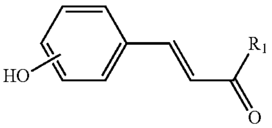

C

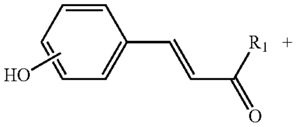

C

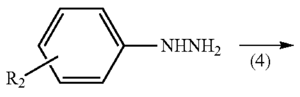

d

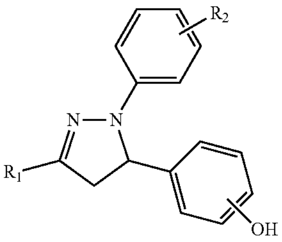

D

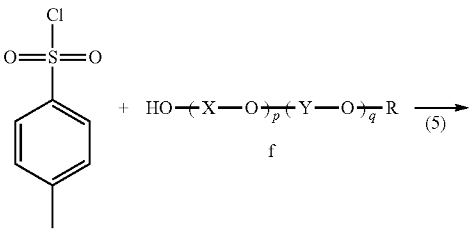

f e

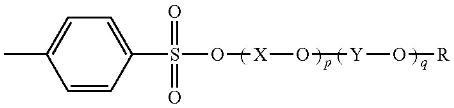

E

-continued

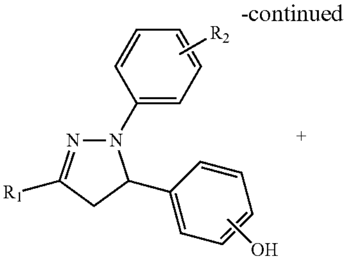

D

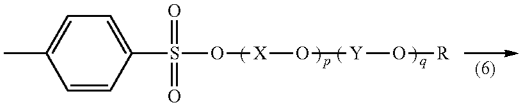

E

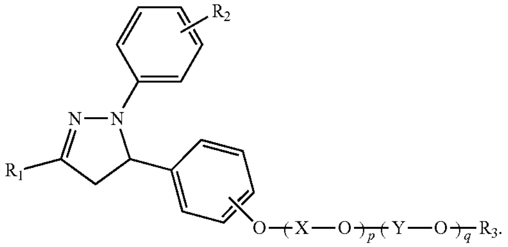

F

The sensitizer of the invention is the improvement and optimization to the existing compound structure. As shown in the above synthesis route, the synthesis involved in the preparation method involves pyrazoline ring structure construction, etherification, etc., all of which are conventional processes in the field of organic chemistry. When the synthesis process and its principle are clarified, the specific process parameters can be easily determined by those skilled in the art. For example, reference may be made to the disclosures described in Chinese Patent application CN1515557A and International patent application WO2009/060235A, which are hereby incorporated by reference in their entireties.

Preferably, in step (1), the solvent used is not particularly limited, as long as it is the conventional organic reagent that can dissolve the reaction reagents and do not participate in the reaction, such as dichloromethane, dichloroethane, toluene, benzene, xylene, etc. The catalyst may be selected from methanesulfonic acid, p-toluenesulfonic acid, and pyridinium p-toluenesulfonate. The reaction temperature is 0 to 50° C., and the reaction time is usually 2 to 10 h.

Preferably, in step (2), the strong base is potassium hydroxide, sodium hydroxide, or the like. The reaction is conducted in an organic solvent, and the type of the solvent is not particularly limited, and is generally an alcohol solvent such as methanol, ethanol, etc. The reaction temperature and reaction time vary slightly depending upon the structure of the raw material c. Generally, the reaction temperature is 0 to 80° C., and the reaction time is usually 2-10 h.

Preferably, in step (3), the reaction is a hydrolysis reaction process. Typically, the intermediate B may be dissolved in an acid-containing hydrocarbon solvent such as dichloromethane, dichloroethane, etc. Said acid may be hydrochloric acid, acetic acid, methanesulfonic acid, and the like. The reaction temperature is 0 to 50° C., and the reaction time is usually 1 to 10 h.

Preferably, in step (5), the type of the solvent used is not particularly limited, as long as it can dissolve the reaction raw materials and have no adverse effects on the reaction, such as dichloromethane, dichloroethane, acetonitrile, N,N-dimethylformamide, etc. The acid-binding agent may be sodium carbonate, sodium hydroxide, potassium carbonate, sodium methoxide, pyridine, triethylamine, and the like. The reaction temperature is 0 to 100° C., and the reaction time is usually 1 to 6 h.

Preferably, in step (6), the type of the solvent used is not particularly limited, as long as it can dissolve the reaction raw materials and have no adverse effects on the reaction, such as acetonitrile, N,N-dimethylformamide, N,N-diethylformamide, etc. The acid-binding agent may be sodium carbonate, sodium hydroxide, potassium carbonate, sodium methoxide, pyridine, triethylamine, and the like. The reaction temperature is 60 to 140° C., and the reaction time is usually 4 to 10 h.

Another aspect of the invention further provides a photocurable composition comprising: (A) an alkali-soluble polymer, (B) a compound having an ethylenically unsaturated double bond, (C) a sensitizer, (D) a photoinitiator, and (E) other auxiliary agent(s), wherein the sensitizer includes the sensitizer represented by Formula (I).

The above EO/PO modified pyrazoline sensitizer of the invention has excellent solubility and an absorption band of 360-400 nm, and is particularly suitable for use as a sensitizer in a photocuring system (especially a system containing a bisimidazole photoinitiator), and has an excellent effect of sensitivity improvement. When the above EO/PO modified pyrazoline sensitizer of the invention is applied in the photosensitive resin composition, the composition has the characteristics such as high compatibility, high photosensitivity, high resolution, high adhesion, and excellent developing property, as well as better hydrophilicity during development, and can significantly reduce the amount of sludges in the developer when it is recycled, so that the developer can be repeated for many times and effectively used.

The EO/PO modified pyrazoline sensitizer of the invention is water-soluble or water-emulsifiable, and this characteristic eliminates or at least reduces the accumulation of drosses and residues in the developer and stripper solutions as well as the deposition of drosses and residues from uncured photoresist on devices and printed circuit boards, and can improve the yield of printed circuit boards.

(A) Alkali-Soluble Polymer

The alkali-soluble polymer can impart a film-forming function to the photosensitive resin composition. As the alkali-soluble polymer, a polymer having such characteristics can be used without particular limitations.

In a preferred embodiment, the alkali-soluble polymer is selected from one or more of the group consisting of (meth)acrylic polymers, styrenic polymers, epoxy polymers, aliphatic polyurethane (meth)acrylate polymers, aromatic polyurethane (meth)acrylate polymers, amide resins, amide epoxy resins, alkyd resins, and phenolic resins.

In a preferred embodiment, the aforementioned alkali-soluble polymer can be obtained by the radical polymerization of polymerizable monomers. The polymerizable monomer includes but is not limited to: polymerizable styrene derivatives substituted at the α-position or at the aromatic ring, such as styrene, vinyltoluene, α-methylstyrene, p-methylstyrene, p-ethylstyrene, and p-chlorostyrene; acrylamide derivatives, such as acrylamide and diacetone acrylamide; ether derivatives of vinyl alcohol, such as acrylonitrile and vinyl n-butyl ether; (meth)acrylic acid derivatives, such as (meth)acrylic acid, α-bromo(meth)acrylic acid, α-chloro(meth)acrylic acid, β-furyl(meth)acrylic acid, and β-styryl(meth)acrylic acid; (meth)acrylate compounds, such as alkyl (meth)acrylate, benzyl (meth)acrylate, phenoxyethyl methacrylate, tetrahydrofurfuryl (meth)acrylate, dimethylaminoethyl (meth)acrylate, diethylaminoethyl (meth)acrylate, glycidyl (meth)acrylate, 2,2,2-trifluoroethyl (meth)acrylate, 2,2,3,3-tetrafluoropropyl (meth)acrylate, 2-ethylhexyl (meth)acrylate, tetrahydrofurfuryl (meth)acrylate, dimethylaminoethyl (meth)acrylate, diethylaminoethyl (meth)acrylate, and glycidyl (meth)acrylate; maleic acid, maleic anhydride, and maleic acid monoesters such as monomethyl maleate, monoethyl maleate, and monoisopropyl maleate; fumaric acid, cinnamic acid, α-cyanocinnamic acid, itaconic acid, crotonic acid, propanoic acid, N-vinylcaprolactam; N-vinylpyrrolidone, etc. These polymerizable monomers may be used alone or in combination of two or more.

From the viewpoint of developing property and adhesion for alkali, in order to improve the developing property and adhesion of the alkali-soluble polymer, it is preferable to use a carboxy-containing alkali-soluble polymer. The aforementioned carboxy-containing alkali-soluble polymer includes but is not limited to: an acrylic resin comprising (meth)acrylic acid as a monomer unit, which introduces a carboxyl group by using (meth)acrylic acid as a monomer unit; a copolymer further comprising alkyl (meth)acrylate as a monomer unit in addition to (meth)acrylic acid; and a copolymer further containing a polymerizable monomer other than (meth)acrylic acid and alkyl (meth)acrylate (such as a monomer having an ethylenically unsaturated group) as a monomer component in addition to (meth)acrylic acid.

In another preferred embodiment, the carboxy-containing alkali-soluble polymer can be obtained by radical polymerization of carboxy-containing polymerizable monomers and other polymerizable monomers, and especially is a (meth)acrylate polymer formed by the copolymerization of (meth)acrylates, ethylenically unsaturated carboxylic acids, and other copolymerizable monomers.

The aforementioned (meth)acrylate includes but is not limited to: methyl (meth)acrylate, ethyl (meth)acrylate, propyl (meth)acrylate, butyl (meth)acrylate, pentyl (meth)acrylate, hexyl (meth)acrylate, heptyl (meth)acrylate, octyl (meth)acrylate, 2-ethylhexyl (meth)acrylate, nonyl (meth)acrylate, decyl (meth)acrylate, undecyl (meth)acrylate, dodecyl (meth)acrylate, cyclohexyl (meth)acrylate, benzyl (meth)acrylate, diethylaminoethyl (meth)acrylate, dimethylaminoethyl (meth)acrylate, hydroxyethyl (meth)acrylate, hydroxypropyl (meth)acrylate, furfuryl (meth)acrylate, glycidyl (meth)acrylate, etc. These (meth)acrylates may be used alone or in combination of two or more.

The aforementioned ethylenically unsaturated carboxylic acid includes but is not limited to: acrylic acid, methacrylic acid, butenoic acid, maleic acid, fumaric acid, and itaconic acid, preferably acrylic acid and methacrylic acid. These ethylenically unsaturated carboxylic acids may be used alone or in combination of two or more.

The aforementioned other copolymerizable monomer includes but is not limited to: (meth)acrylamide, n-butyl (meth)acrylate, styrene, vinyl naphthalene, (meth)acrylonitrile, vinyl acetate, vinyl cyclohexane, etc. These other copolymerizable monomers may be used alone or in combination of two or more.

The aforementioned alkali-soluble polymer may be used alone or in combination of two or more. The two or more alkali-soluble polymers used in combination may be two or more alkali-soluble polymers composed of different copolymerization components, two or more alkali-soluble polymers with different weight average molecular weights, two or more alkali-soluble polymers having different dispersities, etc.

In the photosensitive resin composition of the invention, the weight average molecular weight of the alkali-soluble polymer is not particularly limited, and it should be adapted to the specific application environment. In comprehensive consideration of mechanical strength and alkali developing property, in order to further improve the alkali developing property of the alkali-soluble polymer and the mechanical strength after film formation, preferably, the weight average molecular weight of the alkali-soluble polymer is preferably 15,000 to 200,000, more preferably 30,000 to 150,000, and particularly preferably 30,000 to 120,000. When the weight average molecular weight is greater than 15,000, the developer resistance after exposure tends to be further improved. When the weight average molecular weight is less than 200,000, the development time tends to become shorter, and the compatibility with other components such as photoinitiator can be maintained. The weight average molecular weight of the alkali-soluble polymer is measured by gel permeation chromatography (GPC), and is obtained by conversion using standard curve of standard polystyrene.

From the viewpoint of good alkali developing property, when the acid value of the alkali-soluble resin is relatively small, the development speed of the alkali-soluble resin is relatively slow; when the acid value is relatively large, the adhesion of the alkali-soluble resin is relatively small, and after developing, it is likely to have problems such as reduced storage stability of the composition and increased viscosity. In order to improve the developing property and adhesion of the alkali-soluble polymer, the alkali-soluble polymer has an acid value of preferably 50 to 300 mgKOH/g, more preferably 50 to 250 mgKOH/g, further preferably 70 to 250 mgKOH/g, and particularly preferably 100 to 250 mgKOH/g.

The molecular weight distribution [weight average molecular weight (Mw)/number average molecular weight (Mn)] of the alkali-soluble resin is preferably 1.5 to 6.0, and particularly preferably 1.8 to 3.7. When the molecular weight distribution is within said range, the developing property is excellent.

In 100 parts by weight of the photosensitive resin composition, the content of the alkali-soluble polymer in the composition is preferably 20 to 70 parts by weight, and more preferably 30 to 60 parts by weight. When the content of the alkali-soluble polymer is 20 parts by weight or more, it can ensure that the photosensitive resin composition has an improved durability for plating treatment, etching treatment, etc. When the content is less than 70 parts by weight, it is beneficial to improve the sensitivity of the photosensitive resin composition.

(B) Compound Having an Ethylenically Unsaturated Double Bond

The compound having an ethylenically unsaturated double bond can promote the film formation of the photosensitive resin composition. The compound having an ethylenically unsaturated double bond is not particularly limited, as long as it is a photopolymerizable compound having at least one ethylenically unsaturated bond in the molecule. Preferably, the compound having an ethylenically unsaturated double bond includes but is not limited to one or more of the group consisting of: compounds obtained by reacting α,β-unsaturated carboxylic acids with polyols, bisphenol A-based (meth)acrylate compounds, compounds obtained by reacting α,β-unsaturated carboxylic acids with glycidyl-containing compounds, urethane monomers such as (meth) acrylate compounds having a urethane bond in the molecule, nonylphenoxypolyethyleneoxyacrylates, γ-chloro-β-hydroxypropyl-β'-(meth)acryloyloxyethyl-phthalates, β-hydroxyethyl-β'-(meth)acryloyloxyethyl-phthalates, β-hydroxypropyl-β'-(meth)acryloyloxyethyl-phthalates, benzene dicarboxylic acid compounds, and alkyl (meth)acrylates. Compared with other types of compounds having ethylenically unsaturated double bonds, adopting the several types as above is beneficial to further improve the film-forming property of the photosensitive resin and reduce the cost.

In a preferred embodiment, the aforementioned compound obtained by reacting α,β-unsaturated carboxylic acid with polyol includes but is not limited to one or more of the group consisting of: polyethylene glycol di(meth)acrylate with an ethylene number of 2-14, propylene oxide di(meth) acrylate with an propylene number of 2-14, polyethylene·polypropylene glycol di(meth)acrylate with an ethylene number of 2-14 and an propylene number of 2-14, trimethylolpropane di(meth)acrylate, trimethylolpropane tri (meth)acrylate, EO modified trimethylolpropane tri(meth) acrylate, PO modified trimethylolpropane tri(meth)acrylate, EO,PO modified trimethylolpropane tri(meth)acrylate, tetramethylolmethane tri(meth)acrylate, tetramethylolmethane tetra(meth)acrylate, dipentaerythritol penta(meth)acrylate, dipentaerythritol hexa(meth)acrylate, polypropylene glycol mono(meth)acrylate, polyethylene glycol mono (meth)acrylate, and tripropylene glycol di(meth)acrylate.

In another preferred embodiment, the bisphenol A-based (meth)acrylate compound includes but is not limited to: 2,2-bis{4-[(meth)acryloyloxypolyethoxy]phenyl}propane, 2,2-bis{4-[(meth)acryloyloxypolypropoxy]phenyl}propane, 2,2-bis{4-[(meth)acryloyloxypolybutoxy]phenyl}propane, 2,2-bis{4-[(meth)acryloyloxypolyethoxypolypropoxy] phenyl}propane, etc.

More preferably, the aforementioned 2,2-bis{4-[(meth) acryloyloxypolyethoxy]phenyl}propane includes but is not limited to one or more of the group consisting of: 2,2-bis {4-[(meth)acryloyloxydiethoxy]phenyl}propane, 2,2-bis{4-[(meth)acryloyloxytriethoxy]phenyl}propane, 2,2-bis{4-[(meth)acryloyloxytetraethoxy]phenyl}propane, 2,2-bis{4-[(meth)acryloyloxypentaethoxy]phenyl}propane, 2,2-bis{4-[(meth)acryloyloxyhexaethoxy]phenyl}propane, 2,2-bis{4-[(meth)acryloyloxyheptaethoxy]phenyl}propane, 2,2-bis{4-[(meth)acryloyloxyoctaethoxy]phenyl}propane, 2,2-bis{4-[(meth)acryloyloxynonaethoxy]phenyl}propane, 2,2-bis{4-[(meth)acryloyloxydecaethoxy]phenyl}propane, 2,2-bis{4-[(meth)acryloyloxyundecaethoxy]phenyl}propane, 2,2-bis{4-[(meth)acryloyloxydodecaethoxy]phenyl}propane, 2,2-bis{4-[(meth)acryloyloxytridecaethoxy] phenyl}propane, 2,2-bis{4-[(meth)acryloyloxytetradecaethoxy]phenyl}propane, 2,2-bis{4-[(meth)acryloyloxypentadecaethoxy]phenyl}propane, and 2,2-bis{4-[(meth) acryloyloxyhexadecaethoxy]phenyl}propane.

More preferably, the number of oxyethylene groups in one molecule of the aforementioned 2,2-bis{4-[(meth)acryloyloxypolyethoxy]phenyl}propane is preferably 4-20, and more preferably 8-15. These compounds may be used alone or in combination of two or more.

In a preferred embodiment, the aforementioned (meth) acrylate compound having a urethane bond in the molecule includes but is not limited to: an addition reaction product of (meth)acrylic monomer having an OH group at the β-position with a diisocyanate compound, tris[(meth)acryloyloxytetraethylenediol isocyanate)hexamethylene isocyanurate, EO modified urethane di(meth)acrylate, PO modified urethane di(meth)acrylate, EO,PO modified urethane di(meth)acrylate, etc. Among them, the diisocyanate compound includes but is not limited to one or more of the group consisting of: isophorone diisocyanate, 2,6-toluene diisocyanate, 2,4-toluene diisocyanate, and 1,6-hexamethylene diisocyanate.

In a preferred embodiment, the aforementioned nonylphenoxypolyethyleneoxyacrylate includes but is not limited to one or more of the group consisting of: nonylphenoxytetraethyleneoxyacrylate, nonylphenoxypentaethyleneoxyacrylate, nonylphenoxyhexaethyleneoxyacrylate, nonylphenoxyheptaethyleneoxyacrylate, nonylphenoxyoctaethyleneoxyacrylate, nonylphenoxynonaethyleneoxyacrylate, nonylphenoxydecaethyleneoxyacrylate, and nonylphenoxyundecaethyleneoxyacrylate.

In a preferred embodiment, the aforementioned benzene dicarboxylic acid compound includes but is not limited to one or more of the group consisting of γ-chloro-β-hydroxypropyl-β'-(meth)acryloyloxyethyl phthalate and β-hydroxyalkyl-β'-(meth)acryloyloxyalkyl phthalate.

In a preferred embodiment, the aforementioned alkyl (meth)acrylate is not limited to one or more of the group consisting of: methyl (meth)acrylate, ethyl (meth)acrylate, n-propyl (meth)acrylate, isopropyl (meth)acrylate, n-butyl (meth)acrylate, sec-butyl (meth)acrylate, tert-butyl (meth) acrylate, 2-ethylhexyl (meth)acrylate, phenyl (meth)acrylate, isobornyl (meth)acrylate, hydroxymethyl (meth)acrylate, hydroxyethyl (meth)acrylate, hydroxypropyl (meth) acrylate, 2-hydroxyethyl (meth)acrylate, 2-hydroxypropyl (meth)acrylate, benzyl (meth)acrylate, pentyl (meth)acrylate, tetrahydrofurfuryl (meth)acrylate, isooctyl (meth)acrylate, ethoxylated nonylphenol (meth)acrylate, propylene glycol polypropylene ether di(meth)acrylate, 1,9-nonanediol di(meth)acrylate, 1,10-decanediol di(meth)acrylate, ethoxylated polytetrahydrofurandiol di(meth)acrylate, and ethoxylated polypropylene glycol di(meth)acrylate. More preferably, the alkyl (meth)acrylate includes but is not limited to one or more of the group consisting of: methyl (meth) acrylate, ethyl (meth)acrylate, trimethylolpropane tri(meth) acrylate, ethoxylated trimethylolpropane tri(meth)acrylate, pentaerythritol tri(meth)acrylate, ethoxylated pentaerythritol tetra(meth)acrylate, dipentaerythritol penta(meth)acrylate, and dipentaerythritol hexaacrylate.

From the viewpoint of improving resolution, plating resistance, and adhesion, in order to improve the resolution, plating resistance, and adhesion of the photosensitive resin, preferably, the compound having an ethylenically unsaturated double bond is selected from the bisphenol A-based (meth)acrylate compound and/or the (meth)acrylate compound having an urethane bond in the molecular.

From the viewpoint of improving the sensitivity and resolving degree, in order to improve the sensitivity and resolving degree of the photosensitive resin, preferably, the compound having an ethylenically unsaturated double bond is the bisphenol A-based (meth)acrylate compound.

The commercially available product of the bisphenol A-based (meth)acrylate compound includes but is not limited to: 2,2-bis{4-[(meth)acryloyloxypolyethoxy] phenyl}propane (manufactured by Shin-nakamura Chemical Co. Ltd., BPE-200), 2,2-bis{4-[(meth)acryloyloxypolypropoxy]phenyl)propane (manufactured by Shin-nakamura Chemical Co. Ltd., BPE-5000; manufactured by Hitachi Chemical Co., Ltd., FA-321M), 2,2-bis{4-[(meth)acryloyloxypolybutoxy]phenyl}propane (manufactured by Shin-nakamura Chemical Co. Ltd., BPE-1300), etc.

In a preferred embodiment, in 100 parts by weight of the photosensitive resin composition, the content of the compound having an ethylenically unsaturated double bond (B) is 20 to 50 parts by weight, and more preferably 25 to 45 parts by weight. When the content of the compound having an ethylenically unsaturated double bond is more than 20 parts by weight, the sensitivity and resolving degree of the photosensitive resin composition will be further improved; and when said content is 50 parts by weight or less, the film formation for the photosensitive resin composition is more easy, and the durability against etching treatment is further improved.

First Sensitizer (C)

The aforementioned first sensitizer (C) is one or more of the above EO/PO modified pyrazoline sensitizers, and the structure is as described above.

In order to further improve the sensibilization of the photocurable composition, preferably, in 100 parts by weight of the photosensitive resin composition, the content of the first sensitizer (C) (the EO/PO modified pyrazoline sensitizer) is 0.001 to 10 parts by weight, and preferably 0.005 to 5 parts by weight. If the content is too small, there is a defect of reduced photosensitivity; and if the content is too large, there is a defect that the photoresist pattern tends to become wider than the line width of the photomask. Limiting the amount of the sensitizer to the above range is beneficial to improve the photosensitivity and definiteness of the photocurable composition.

Other Photoinitiators and/or Second Sensitizer (D)

In addition to the above EO/PO modified pyrazoline sensitizer, optionally, the above photosensitive resin composition may further comprise a photoinitiator and other kinds of sensitizers, and the photoinitiator may also adopt those commonly used in the art. The aforementioned photoinitiator and/or second sensitizer includes but is not limited to one or more of the group consisting of: bisimidazole organic compounds, acridine organic compounds, aromatic ketone organic compounds, anthraquinone organic compounds, benzoin and benzoin alkyl ether organic compounds, oxime ester organic compounds, triazine organic compounds, coumarin organic compounds, and thioxanthone organic compounds.

In a preferred embodiment, the bisimidazole compounds include but are not limited to: 2,2'-bis(orthchlorophenyl)-4, 4',5,5'-tetraphenyl-diimidazole, 2,2',5-tris(orthchlorophenyl)-4-(3,4-dimethoxyphenyl)-4',5'-diphenyl-1,1'-diimidazole, 2,2',5-tris(2-fluorophenyl)-4-(3,4-dimethoxyphenyl)-4',5'-diphenyl-diimidazole, 2,2'-bis(2,4-dichlorophenyl)-4, 4',5,5'-tetraphenyl-diimidazole, 2,2'-bis(2-fluorophenyl)-4-(orthchlorophenyl)-5-(3,4-dimethoxyphenyl)-4',5'-diphenyl-diimidazole, 2,2'-bis(2-fluorophenyl)-4,4',5,5'-tetraphenyl-diimidazole, 2,2'-bis(2-methoxyphenyl)-4,4',5, 5'-tetraphenyl-diimidazole, 2,2'-bis(2-chloro-5-nitrophenyl)-4,4'-bis(3,4-dimethoxyphenyl)-5,5'-bis (orthchlorophenyl)-diimidazole, 2,2'-bis(2-chloro-5-nitrophenyl)-4-(3,4-dimethoxyphenyl)-5-(orthchlorophenyl)-4',5'-diphenyl-diimidazole, 2,2'-bis(2,4-dichlorophenyl)-4,4'-bis(3,4-dimethoxyphenyl)-5,5'-bis (orthchlorophenyl)-diimidazole, 2-(2,4-dichlorophenyl)-4-(3,4-dimethoxyphenyl)-2',5-bis(orthchlorophenyl)-4',5'-diphenyl-diimidazole, 2-(2,4-dichlorophenyl)-2'-(orthchlorophenyl)-4,4',5,5'-tetraphenyl-diimidazole, and 2,2'-bis(2,4-dichlorophenyl)-4,4',5,5'-tetraphenyl-diimidazole. These bisimidazole compounds may be used alone or in combination of two or more.

In a preferred embodiment, the acridine compounds include but are not limited to: 9-phenylacridine, 9-paramethylphenylacridine, 9-metamethylphenylacridine, 9-orthchlorophenylacridine, 9-orthofluorophenylacridine, 1,7-bis(9-acridinyl)heptane, 9-ethylacridine, 9-(4-bromophenyl) acridine, 9-(3-chlorophenyl)acridine, 1,7-bis(9-acridine)

heptane, 1,5-bis(9-acridinepentane), and 1,3-bis(9-acridine) propane. These acridine compounds may be used alone or in combination of two or more.

In a preferred embodiment, the aromatic ketone compounds include but are not limited to: acetophenone, 2,2-dimethoxy-2-phenylacetophenone, 2,2-diethoxy phenylacetophenone, 1,1-dichloroacetophenone, benzophenone, 4-benzoyl diphenyl sulfide, 4-benzoyl-4'-methyl diphenyl sulfide, 4-benzoyl-4'-ethyl diphenyl sulfide, 4-benzoyl-4'-propyl diphenyl sulfide, 4,4'-bis(diethylamino)benzophenone, 4-paratolylthiobenzophenone, 2,4,6-trimethylbenzophenone, 4-methylbenzophenone, 4,4'-bis(dimethylamino) benzophenone, 4,4'-bis(methyl, ethylamino)benzophenone, acetophenone dimethyl ketal, benzil dimethyl ketal, α,α'-dimethylbenzyl ketal, α,α'-diethoxyacetophenone, 2-hydroxy-2-methyl-1-phenylacetone, 1-hydroxycyclohexylbenzophenone, 2-hydroxy-2-methyl-1-parahydroxyethyl ether phenylacetone, 2-methyl 1-(4-methylthiophenyl)-2-morpholine 1-acetone, 2-benzyl-2-dimethylamino-1-(4-morpholinephenyl) 1-butanone, phenylbis(2,4,6-trimethylbenzoyl)phosphine oxide, 2,4,6(trimethylbenzoyl) diphenylphosphine oxide, 2-hydroxy-1-{3-[4-(2-hydroxy-2-methyl-propionyl)-phenyl]-1,1,3-trimethyl-inden-5-yl}-2-methylacetone, 2-hydroxy-1-1{-[4-(2-hydroxy-2-methyl-propionyl)-phenyl]-1,3,3-trimethyl-inden-5-yl}-2-methylacetone, 1-(4-isopropylphenyl)-2-hydroxy-2-methylpropan-1-one, and 4-(2-hydroxyethoxy)-phenyl-(2-hydroxy-2-propyl)one. These aromatic ketone compounds may be used alone or in combination of two or more.

In a preferred embodiment, the anthraquinone compounds include but are not limited to: 2-phenylanthraquinone, 2,3-diphenylanthraquinone, 1-chloroanthraquinone, 2-methylanthraquinone, 2,3-dimethylanthraquinone, 2-ethylanthracene-9,10-diethyl ester, 1,2,3-trimethylanthracene-9,10-dioctyl ester, 2-ethylanthracene-9,10-bis(4-chlorobutyric acid methyl ester), 2-{3-[(3-ethyloxetan-3-yl)methoxy]-3-oxopropyl}anthracene-9,10-diethyl ester, 9,10-dibutoxyanthracene, 9,10-diethoxy-2-ethylanthracene, 9,10-bis(3-chloropropoxy) anthracene, 9,10-bis(2-hydroxyethylthio) anthracene, and 9,10-bis(3-hydroxy-1-propylthio) anthracene. These anthraquinone compounds may be used alone or in combination of two or more.

In a preferred embodiment, the benzoin and benzoin alkyl ether compounds include but are not limited to: benzoin methyl ether, benzoin ethyl ether, and benzoin phenyl ether. These benzoin and benzoin alkyl ether compounds may be used alone or in combination of two or more.

In a preferred embodiment, the oxime ester compounds include but are not limited to: 1-(4-phenylthiophenyl)-n-octane-1,2-dione-2-benzoic acid oxime ester, 1-[6-(2-methylbenzoyl)-9-ethylcarbazol-3-yl]-ethane-1-one-acetic acid oxime ester, 1-[6-(2-methylbenzoyl)-9-ethylcarbazol-3-yl]-butane-1-one-acetic acid oxime ester, 1-[6-(2-methylbenzoyl)-9-ethylcarbazol-3-yl]-propane-1-one-acetic acid oxime ester, 1-[6-(2-methylbenzoyl)-9-ethylcarbazol-3-yl]-1-cyclohexyl-methane-1-one-acetic acid oxime ester, 1-[6-(2-methylbenzoyl)-9-ethylcarbazol-3-yl]-(3-cyclopentyl)-propane-1-one-acetic acid oxime ester, 1-(4-phenylthiophenyl)-(3-cyclopentyl)-propane-1,2-dione-2-benzoic acid oxime ester, 1-(4-phenylthiophenyl)-(3-cyclohexyl)-propane-1,2-dione-2-cyclohexylformic acid oxime ester, 1-[6-(2-methylbenzoyl)-9-ethylcarbazol-3-yl]-(3-cyclopentyl)-propane-1,2-dione-2-acetic acid oxime ester, 1-(6-orthomethylbenzoyl-9-ethylcarbazol-3-yl)-(3-cyclopentyl)-propane-1,2-dione-2-benzoic acid oxime ester, 1-(4-benzoyldiphenyl sulfide)-(3-cyclopentylacetone)-1-oxime acetate, 1-(6-orthomethylbenzoyl-9-ethylcarbazol-3-yl)-(3-cyclopentylacetone)-1-oxime cyclohexylformate, 1-(4-benzoyldiphenyl sulfide)-3-cyclopentylacetone)-1-oxime cyclohexylformate, 1-(6-orthomethylbenzoyl-9-ethylcarbazol-3-yl)-(3-cyclopentyl)-propane-1,2-dione-2-orthomethylbenzoic acid oxime ester, 1-(4-phenylthiophenyl)-(3-cyclopentyl)-propane-1,2-dione-2-cyclohexylformic acid oxime ester, 1-(4-thiopheneformyl-diphenyl sulfide-4'-yl)-3-cyclopentyl-propane-1-one-acetic acid oxime ester, 1-(4-benzoyldiphenyl sulfide)-(3-cyclopentyl)-propane-1,2-dione-2-oxime acetate, 1-(6-nitro-9-ethylcarbazol-3-yl)-3-cyclohexyl-propane-1-one-acetic acid oxime ester, 1-(6-orthomethylbenzoyl-9-ethylcarbazol-3-yl)-3-cyclohexyl-propane-1-one-acetic acid oxime ester, 1-(6-thiopheneformyl-9-ethylcarbazol-3-yl)-(3-cyclohexylacetone)-1-oxime acetate, 1-(6-furanfuroyl-9-ethylcarbazol-3-yl)-(3-cyclopentylacetone)-1-oxime acetate, 1,4-diphenylpropane-1,3-dione-2-acetic acid oxime ester, 1-(6-furoyl-9-ethylcarbazol-3-yl)-(3-cyclohexyl)-propane-1,2-dione-2-acetic acid oxime ester, 1-(4-phenylthiophenyl)-(3-cyclohexyl)-propane-1,2-dione-2-acetic acid oxime ester, 1-(6-furanfuroyl-9-ethylcarbazol-3-yl)-(3-cyclohexylacetone)-1-oxime acetate, 1-(4-phenylthiophenyl)-(3-cyclohexyl)-propane-1,2-dione-3-benzoic acid oxime ester, 1-(6-thiopheneformyl-9-ethylcarbazol-3-yl)-(3-cyclohexyl)-propane-1,2-dione-2-acetic acid oxime ester, 2-[benzoyloxy)iminol]-1-phenylpropane-1-one, 1-phenyl-1,2-propanedione-2-(oxoacetyl)oxime, 1-(4-phenylthiophenyl)-2-(2-methylphenyl)-ethane-1,2-dione-2-acetic acid oxime ester, 1-(9,9-dibutyl-7-nitrofluoren-2-yl)-3-cyclohexyl-propane-1-one-acetic acid oxime ester, 1-{4-[4-(thiophene-2-formyl)phenylthio]phenyl}-3-cyclopentylpropane-1,2-dione-2-acetic acid oxime ester, 1-[9,9-dibutyl-2-yl]-3-cyclohexylpropylpropane-1,2-dione-2-acetic acid oxime ester, 1-[6-(2-benzoyloxyimino)-3-cyclohexylpropyl-9-ethylcarbazol-3-yl]octane-1,2-dione-2-benzoic acid oxime ester, 1-(7-nitro-9,9-diallylfluoren-2-yl)-1-(2-methylphenyl) ketone-acetic acid oxime ester, 1-[6-(2-methylbenzoyl)-9-ethylcarbazol-3-yl]-3-cyclopentyl-propane-1-one-benzoic acid oxime ester, 1-[7-(2-methylbenzoyl)-9,9-dibutylfluoren-2-yl]-3-cyclohexylpropane-1,2-dione-2-acetic acid oxime ester, and 1-[6-(furan-2-formyl)-9-ethylcarbazol-3-yl]-3-cyclohexylpropane-1,2-dione-2-ethoxyformyl oxime ester. These oxime ester compounds may be used alone or in combination of two or more.

In a preferred embodiment, the triazine compounds include but are not limited to: 2-(4-ethylbiphenyl)-4,6-bis(trichloromethyl)-1,3,5-triazine, 2-(3,4-methyleneoxyphenyl)-4,6-bis(trichloromethyl)-1,3,5-triazine, 3-{4-[2,4-bis(trichloromethyl)-s-triazin-6-yl]phenylthio}propionic acid, 1,1,1,3,3,3-hexafluoroisopropyl 3-{4-[2,4-bis(trichloromethyl)-s-triazin-6-yl]phenylthio}propionate, ethyl 2-{4-[2,4-bis(trichloromethyl)-s-triazin-6-yl]phenylthio}acetate, 2-ethoxyethyl 2-{4-[2,4-bis(trichloromethyl)-s-triazin-6-yl]phenylthio}acetate, cyclohexyl 2-{4-[2,4-bis(trichloromethyl)-s-triazin-6-yl]phenylthio}acetate, benzyl 2-{4-[2,4-bis(trichloromethyl)-s-triazin-6-yl]phenylthio}acetate, 3-{chloro-4-[2,4-bis(trichloromethyl)-s-triazin-6-yl]phenylthio}propionic acid, 2,4-bis(trichloromethyl)-6-p-methoxystyryl-s-triazine, 2,4-bis(trichloromethyl)-6-(1-p-dimethylaminophenyl)-1,3-butadienyl-s-triazine, and 2-trichloromethyl-4-amino-6-p-methoxystyryl-s-triazine. These triazine compounds may be used alone or in combination of two or more.

In a preferred embodiment, the coumarin compounds are not limited to: 3,3'-carbonylbis(7-diethylaminocoumarin), 3-benzoyl-7-diethylaminocoumarin, 3,3'-carbonylbis(7-methoxycoumarin), 7-diethylamino-4-methylcoumarin, 3-(2-benzothiazole)-7-(diethylamino)coumarin, 7-(diethylamino)-4-methyl-2H-1-benzopyran-2-one[7-(diethylamino)-4-methylcoumarin], and 3-benzoyl-7-methoxycoumarin. These coumarin compounds may be used alone or in combination of two or more.

In a preferred embodiment, the thioxanthone compounds include but are not limited to: thioxanthone, 2,4-dimethylthioxanthone, 2,4-diethylthioxanthone, 2,4-diisopropylthioxanthone, 2-chlorothioxanthone, 1-chloro-4-propoxythioxanthone, isopropylthioxanthone, and diisopropylthioxanthone. These thioxanthone compounds may be used alone or in combination of two or more.

In a preferred embodiment, the coumarin compounds include but are not limited to: 3,3'-carbonylbis(7-diethylaminocoumarin), 3-benzoyl-7-diethylaminocoumarin, 3,3'-carbonylbis(7-methoxycoumarin), 7-diethylamino-4-methylcoumarin, 3-(2-benzothiazole)-7-(diethylamino) coumarin, 7-(diethylamino)-4-methyl-2H-1-benzopyran-2-one[7-(diethylamino)-4-methylcoumarin], and 3-benzoyl-7-methoxycoumarin. These coumarin compounds may be used alone or in combination of two or more.

In a preferred embodiment, the thioxanthone compounds include: thioxanthone, 2,4-dimethylthioxanthone, 2,4-diethylthioxanthone, 2,4-diisopropylthioxanthone, 2-chlorothioxanthone, 1-chloro-4-propoxythioxanthone, isopropylthioxanthone, and diisopropylthioxanthone. These thioxanthone compounds may be used alone or in combination of two or more.

In a preferred embodiment, in 100 parts by weight of the photosensitive resin composition, the total content of other photoinitiators and/or second sensitizer (D) is 0.01 to 10 parts by weight.

(E) Other Auxiliary Agents

In addition to the above components, optionally, the photosensitive resin composition of the invention may further comprise an appropriate amount of other auxiliary agents as needed. In a preferred embodiment, the auxiliary agent includes but is not limited to one or more of hydrogen donors, dyes, pigments, light chromogenic reagents, fillers, plasticizers, stabilizers, coating aids, and stripping promoters.

In the above photocurable composition, the specific type of the hydrogen donor is not particularly limited. Preferably, the hydrogen donor includes but is not limited to amine compounds, carboxylic acid compounds, mercapto-containing organosulfur compounds, or alcohol compounds. These compounds may be used alone or in combination of two or more of them. Optionally, the hydrogen donor includes but is not limited to: triethanolamine, methyl 4-dimethylaminobenzoate, 4,4'-bis(dimethylamino)benzophenone, 4,4'-bis (diethylamino)benzophenone, phenylthioacetic acid, methylphenylthioacetic acid, ethylphenylthioacetic acid, dimethoxyphenylthioacetic acid, chlorophenylthioacetic acid, dichlorophenylthioacetic acid, N-phenylglycine, phenoxyacetic acid, naphthylthioacetic acid, N-naphthylglycine, naphthyloxyacetic acid, 2-mercaptobenzothiazole (MBO), 2-mercaptobenzimidazole (MBI), dodecyl mercaptan, ethylene glycol bis(3-mercaptobutyrate), etc.

In a preferred embodiment, the dye, pigment, and light chromogenic reagent include but are not limited to: tris(4-dimethylaminophenyl)methane (i.e., Leuco Crystal Violet, LCV), tris(4-dimethylamino-2methylphenyl)methane, fluorane dyes, toluenesulfonic acid monohydrate, Basic Fuchsin, phthalocyanine dyes (such as phthalocyanine green and/or phthalocyanine blue), auramine base, parafuchsin, Crystal Violet, Methyl Orange, Nile Blue 2B, Victoria Blue, Malachite Green, Diamond Green, Basic Blue 20, Brilliant Green, Eosin, Ethyl Violet, Erythrosine Sodium B, Methyl Green, phenolphthalein, Alizarin Red S, thymolphthalein, Methyl Violet 2B, Quinadine Red, Rose Bengal Sodium Agar, Mitaniel Yellow, thymolsulfophthalein, Xylenol Blue, Methyl Orange, Orange IV, dithizone, 2,7-dichlorofluorescein, Paramethyl Red, Congo Red, Benzopurpurin 4B, α-Naphthyl Red, phenacetin, Methyl Violet, Victoria Pure Blue BOH, Rhodamine 6G, diphenylamine, dibenzylaniline, triphenylamine, N,N-diethylaniline, di-p-phenylenediamine, p-toluidine, benzotriazole, methyl benzotriazole, 4,4'-biphenyldiamine, o-chloroaniline, White Crystal Violet, White Malachite Green, White Aniline, White Methyl Violet, azo-based dyes, and titanium dioxide. These dyes, pigments, and light chromogenic reagents may be used alone or in combination of two or more.

In a preferred embodiment, the filler includes but is not limited to: fillers such as silica, alumina, talc, calcium carbonate, barium sulfate, etc. (excluding the above-mentioned inorganic pigments). The filler may be used alone or in combination of two or more.

In a preferred embodiment, the plasticizer includes but is not limited to: phthalates (such as dibutyl phthalate, diheptyl phthalate, dioctyl phthalate, and diallyl phthalate), glycol esters (such as triethylene glycol diacetate and tetraethylene glycol diacetate), sulfonamide organic compounds (such as p-toluenesulfonamide, benzenesulfonamide, and n-butylbenzenesulfonamide), phosphate organic compounds (such as triphenyl phosphate, trimethyl phosphate, triethyl phosphate, triphenyl phosphate, tritolyl phosphate, trixylyl phosphate, tolyl diphenyl phosphate, trixylyl phosphate, 2-naphthyl diphenyl phosphate, tolyl di-2,6-xylyl phosphate, aromatic condensed phosphate, tris(chloropropyl) phosphate, tris(tribromo-neopentyl) phosphate, halogen-containing condensed phosphate), alcohol ester organic compounds (such as triethylene glycol dicaprylate, triethylene glycol di(2-ethylhexanoate), and tetraethylene glycol diheptanoate), diethyl sebacate, dibutyl suberate, tris(2-ethylethyl) phosphate, Brij30 ($C_{12}H_{25}(OCH_2CH_2)_4OH$), and Brij35 ($C_{12}H_{25}(OCH_2CH_2)_{20}OH$), etc. In the above photocurable composition, the plasticizer may be used alone or in combination of two or more.

In a preferred embodiment, the stabilizer includes but is not limited to: hydroquinone, 1,4,4-trimethyl-diazobicyclo (3.2.2)-non-2-ene-2,3-dioxide, 1-phenyl-3-pyrazolidinone, p-methoxyphenol, alkyl and aryl-substituted hydroquinone and quinone, tert-butylcatechol, 1,2,3-benzenetriol, copper resinate, naphthylamine, β-naphthol, cuprous chloride, 2,6-di-tert-butyl-p-cresol, phenothiazine, pyridine, nitrobenzene, dinitrobenzene, p-toluquinone, and chloranil, etc. In the above photocurable composition, the stabilizer may be used alone or in combination of two or more.

In a preferred embodiment, the coating aid includes but is not limited to: acetone, methanol, methyl alcohol, ethyl alcohol, isopropyl alcohol, methyl ethyl ketone, propylene glycol monomethyl ether acetate, ethyl lactate, cyclohexanone, γ-butyrolactone, dichloromethane, etc. In the above photocurable composition, the coating aid may be used alone or in combination of two or more.

In a preferred embodiment, the stripping promoter includes but is not limited to: benzenesulfonic acid, toluenesulfonic acid, xylenesulfonic acid, phenolsulfonic acid, alkyl (such as methyl, propyl, heptyl, octyl, decyl, dodecyl) benzene sulfonic acid, etc. In the above photocurable composition, the stripping promoter may be used alone or in combination of two or more.

In a preferred embodiment, in 100 parts by weight of the photosensitive resin composition, the content of other auxiliary agents is 1 to 10 parts by weight.

Yet another aspect of the invention further provides the use of the ethoxy/propoxy modified pyrazoline organic compound represented by Formula (I) in the field of photocuring.

Due to the introduction of $—CH_2—CH_2—O(EO)$ and/or $—CH(CH_3)—CH_2—O(PO)$, the above EO/PO modified pyrazoline organic compound has excellent water solubility or water emulsibility. Moreover, it is solid and thus it is convenient to add and use. At the same time, the structure represented by Formula (I) has an absorption band of 360-400 nm and is especially suitable for use as sensitizer in a photocuring system (such as a system containing bisimidazole photoinitiator), and can greatly improve the photosensitivity of the photocuring system. In view of this, the EO/PO modified pyrazoline organic compound with the above structure has high sensitivity enhancements, small usage amounts, and convenience to add and use.

<Dry Film and Wet Film Uses>

The photosensitive resin composition of the invention can be prepared into a dry film (i.e., a photosensitive resin laminate), and used to the manufacture of printed circuit boards, protective patterns, conductor patterns, lead frames, and semiconductor packages, to form required patterns on the different substrates through different processes.

The photosensitive resin composition of the invention can also be directly coated to the corresponding substrate in each corresponding manufacturing step by a wet film coater, that is, applied as a wet film to the manufacture of printed circuit boards, protective patterns, conductor patterns, lead frames, and semiconductor packages, to form required patterns on the different substrates through different processes.

Dry Film Use

The dry film of the present invention (i.e., the photosensitive resin laminate) comprises: a photosensitive resin layer formed of the photosensitive resin composition and a support that supports the photosensitive resin layer.

Generally, the preparation of the dry film includes: coating the photosensitive resin composition on the support and drying to form the photosensitive resin layer; optionally, adhering a cover film (protective layer) as needed. Preferably, the drying condition in the above drying step is drying at 60 to 100° C. for 0.5 to 15 min. The thickness of the photosensitive resin layer is preferably 5 to 95 μm. The thickness of the photosensitive resin includes but is not limited to the above range, and limiting it to the above range is beneficial to improve its insulating property and resolving property. More preferably, the thickness of the photosensitive resin is 10 to 50 μm, and further preferably 15 to 30 μm.

As the support, specific examples may be various types of plastic films, such as polyethylene terephthalate, polyethylene naphthalate, polypropylene, polyethylene, cellulose acetate, polyalkyl methacrylate, methacrylate copolymer, polyvinyl chloride, polyvinyl alcohol, polycarbonate, polystyrene, cellophane, vinyl chloride copolymer, polyamide, polyimide, vinyl chloride-vinyl acetate copolymer, polytetrafluoroethylene, and polytrifluoroethylene. In addition, composite materials composed of two or more materials can also be used. It is preferably to use polyethylene terephthalate having excellent light transmittance. The thickness of the support is preferably 5-150 μm, and more preferably 10-50 μm.

The coating manner of the photosensitive resin composition is not particularly limited. For example, conventional methods such as spray coating, rotary coating, spin coating, slit coating, compression coating, curtain coating, dye coating, line coating, blade coating, roll coating, knife coating, spray coating, and dip coating may be used.

In a preferred embodiment, the invention provides the use of the above dry film in the manufacture of a printed circuit board, including:

(1) Laminating process laminating the photosensitive resin laminate on a substrate;
(2) Exposure process: exposing the photosensitive resin layer in the photosensitive resin laminate by irradiating an active light in an image form to perform the photocuring of the exposed portion;
(3) Development process: removing the unexposed portion of the photosensitive resin layer using a developer, to form a protective pattern;
(4) Conductor pattern formation process: etching or plating the portion of the surface of the copper clad laminate or flexible substrate that is not covered by the protective pattern;
(5) Peeling process: peeling the protective pattern from the copper clad laminate or flexible substrate.

In a preferred embodiment, the substrate used in the laminating process includes but is not limited to one or more of copper clad laminates, flexible substrates, metal plates, metal clad insulating plates, and wafers with large scale integrated circuits.

The invention provides the use of the above dry film in the manufacture of a semiconductor package. When the photosensitive resin laminate is laminated on a metal in the laminating process, the portion not covered by the protective pattern is etched in the conductor pattern formation process. When the photosensitive resin laminate is laminated on a wafer with large scale integrated circuits in the laminating process, the portion not covered by the protective pattern is plated in the conductor pattern formation process.

Wet Film Use

The photosensitive resin composition of the invention can be directly coated on a substrate by a wet film method, to be used in the manufacture of printed circuit boards, protective patterns, conductor patterns, lead frames, semiconductor packages, etc.

Without limitation, the photosensitive resin composition may be coated on the substrate by a conventional method such as roll coating, knife coating, spray coating, and dip coating, and dried to form a photosensitive resin layer.

After the photosensitive resin layer is formed on the substrate, the subsequent processes such as exposure process, development process, conductor pattern formation process, and peeling process can all be performed with reference to the manners in the dry film use.

In the exposure process, examples of the exposure can include a mask exposure method (a method in which the negative or positive mask pattern of the wiring pattern emits the active light in an image form), and a projection exposure method. A direct drawing exposure method in which the active light is irradiated in an image form (such as the direct imaging exposure method by laser and the digital optical processing exposure method) can also be used. As the light source of active light, well-known light sources can be used, for example light sources effectively emitting ultraviolet rays such as carbon arc lamp, mercury vapor arc lamp, ultra-high pressure indicator lamp, high pressure indicator lamp, xenon lamp, gas laser (such as argon laser), solid laser (such as YAG laser), semiconductor laser, and gallium nitride-based blue-violet laser. In addition, light sources effectively emitting visible light, such as floodlight for photography and fluorescent lamp, can also be used. For the photosensitive resin composition of the invention, the type of the light source of active light is not particularly limited, and the exposure amount is preferably 10 to 1,000 mJ/$cm^2$.

In the development process, the unexposed portion of the photosensitive resin layer is removed by a developer. When there is a support on the photosensitive resin layer, the support can be first removed using an automatic stripper or the like, and then the unexposed portion can be removed using a developer (such as an alkaline aqueous solution, an aqueous developer, an organic solvent, etc.). Preferably, the alkaline aqueous solution includes but is not limited to 0.1-5 wt % sodium carbonate solution, 0.1-5 wt % potassium carbonate solution, or 0.1-5 wt % sodium hydroxide solution. The pH value is preferably 9 to 11. More preferably, the aforementioned alkaline aqueous solution further comprises one or more of surfactants, defoamers, or organic solvents. The development method includes but is not limited to conventional methods such as dipping, spraying, and brushing.

In the etching treatment, the resist pattern (i.e., protective pattern) formed on the substrate is used as a mask, to etch and remove the uncovered conductor layer of the substrate for circuit formation, thereby forming a conductor pattern. The method for the etching treatment can be selected according to the conductor layer to be removed. For example, examples of the etching solution may include a copper oxide solution, an iron oxide solution, an alkali etching solution, a hydrogen peroxide-based etching solution, etc.

In the plating treatment, the resist pattern formed on the substrate is used as a mask, to plate copper, tin solder, and the like on the uncovered insulating plate of the substrate for circuit formation. After the plating treatment, the resist pattern is removed to form a conductor pattern. The method for the plating treatment includes but is not limited to the electroplating treatment or electroless plating treatment, and the electroless plating treatment is preferable. More preferably, the electroless plating treatment includes but is not limited to: copper plating (copper sulfate plating and/or copper pyrophosphate plating), tin solder plating (such as high-throw solder plating), nickel plating (Watt bath (nickel sulfate-nickel chloride) plating and/or nickel sulfamate plating), or gold plating (hard gold plating and/or soft gold plating).

The removal of the resist pattern can be performed by peeling using an aqueous solution that is more alkaline than the alkaline aqueous solution used in the development process. As an example of a strong alkaline aqueous solution, for example, 1 to 10 wt % sodium hydroxide aqueous solution can be used.

The subject application is further described in detail below with reference to specific examples, which cannot be understood as limiting the claimed scope in the subject application.

1. Preparation of EO/PO Modified Pyrazoline Sensitizers

1.1 Preparation of Product C1

1.1.1 Preparation of Intermediate A

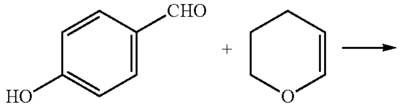

-continued

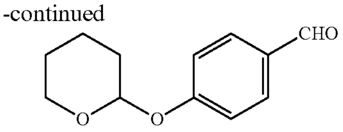

To a four-necked flask 183.1 g of p-hydroxybenzaldehyde, 5.0 g of pyridinium p-toluenesulfonate, and 300.0 mL of dichlorethane were successively added. At a controlled temperature of 45±5° C., 126.0 g of dihydropyran was dropwise added over about 1 h. After the dropwise addition was completed, the system was stirred for another 2 h. The reaction process was under the central control by HPLC, and when the residual p-hydroxybenzaldehyde was less than 1%, the heat preservation was terminated. To the reaction system 52.0 g of 30% sodium hydroxide aqueous solution was dropwise added slowly, and the aqueous layer was separated. The lower organic layer was washed once with 100.0 g of pure water, and subjected to rotary evaporation to remove dichloromethane, to obtain 275.2 g of Intermediate A with a purity of 98.12%, which was directly used in the next reaction.

LCMS was used to confirm the structure of Intermediate A. By means of the software accompanied with the instrument, 207 and 208 molecular fragment peaks were obtained in the mass spectrometry analysis. The molecular weight of the product is 206, consistent with T+1 and T+2.

1.1.2 Preparation of Intermediate B

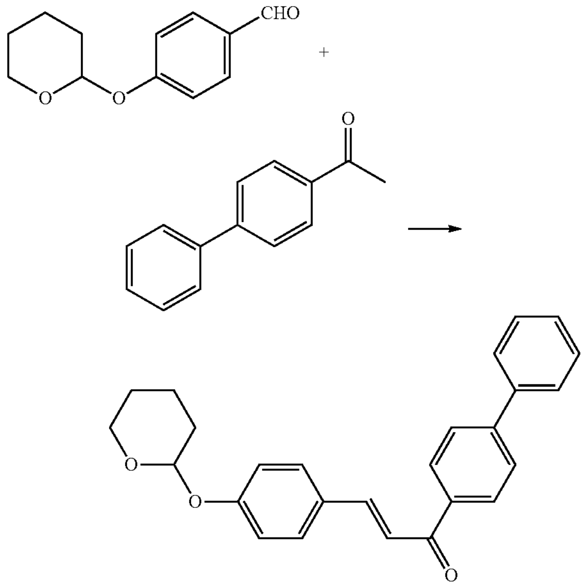

To a four-necked flask 247.1 g of Intermediate A, 235.2 g of phenylacetophenone, and 300.0 mL of methanol were successively added. At a controlled temperature of 25±5° C., 80.0 g of 40% sodium hydroxide aqueous solution was dropwise added over about 2 h. After the dropwise addition was completed, the system was stirred for another 6 h. The reaction process was under the central control by HPLC, and when the residual phenylacetophenone was less than 1%, the heat preservation was terminated. The system was filtered, to obtain 415.6 g of Intermediate B with a purity of 93.65%, which was directly used in the next reaction.

LCMS was used to confirm the structure of Intermediate B. By means of the software accompanied with the instrument, 385 and 386 molecular fragment peaks were obtained in the mass spectrometry analysis. The molecular weight of the product is 384, consistent with T+1 and T+2.

1.1.3 Preparation of Intermediate C

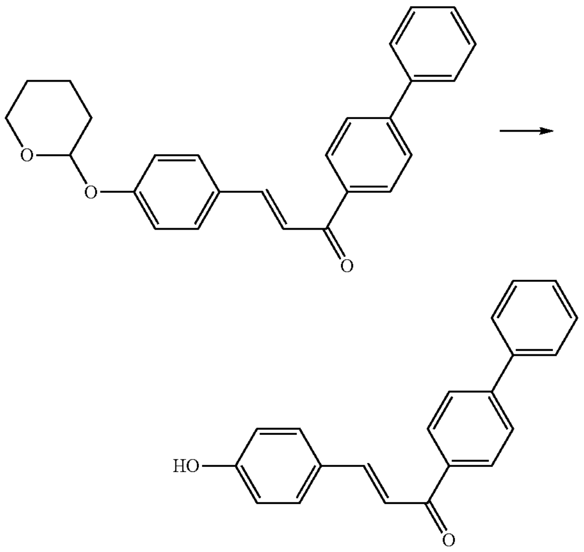

To a four-necked flask 384.4 g of Intermediate B, 50.0 g of 37% concentrated hydrochloric acid, and 500.0 mL of dichloroethane were successively added, and stirred at a controlled temperature of 25±5° C. for another 6 h. The reaction process was under the central control by HPLC, and when the residual Intermediate B was less than 1%, the heat preservation was terminated. The system was filtered and dried, to obtain 210.5 g of Intermediate C with a purity of 98.95%.

LCMS was used to confirm the structure of Intermediate B. By means of the software accompanied with the instrument, 301 and 302 molecular fragment peaks were obtained in the mass spectrometry analysis. The molecular weight of the product is 300, consistent with T+1 and T+2.

1.1.4 Preparation of Intermediate D

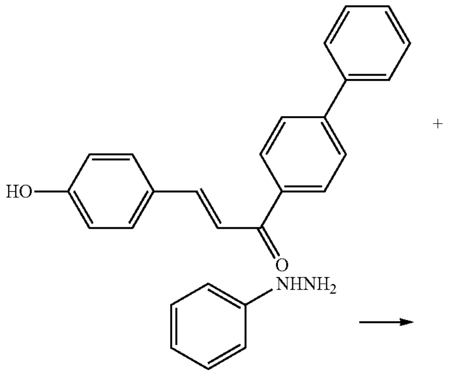

-continued

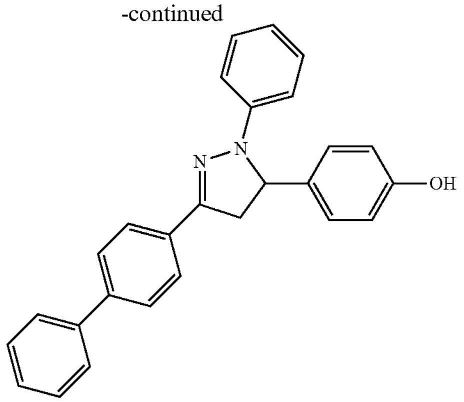

To a four-necked flask 180.0 g of Intermediate C and 500.0 mL of glacial acetic acid were successively added. At a controlled temperature of 50±5° C., 108.0 g of phenylhydrazine was dropwise added over about 2 h. After the dropwise addition was completed, the system was stirred for another 8 h. The system was filtered, subjected to recrystallization with methanol, and dried, to obtain 214.5 g of Intermediate D with a purity of 99.65%.

LCMS was used to confirm the structure of Intermediate B. By means of the software accompanied with the instrument, 391 and 392 molecular fragment peaks were obtained in the mass spectrometry analysis. The molecular weight of the product is 390, consistent with T+1 and T+2.

1.1.5 Preparation of Intermediate E

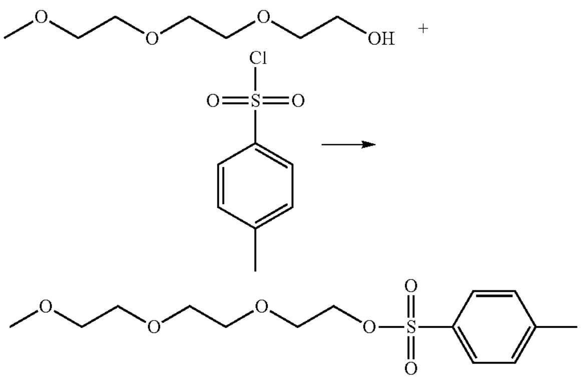

To a four-necked flask 56.1 g of p-toluenesulfonyl chloride, 50.0 g of triethylene glycol monomethyl ether, 200.0 g of dichloromethane, and 0.5 g of 4-dimethylaminopyridine were successively added. After warming to 30° C., 34.0 g of triethylamine was dropwise added over about 30 min. After the dropwise addition was completed, the reaction was conducted under heat preservation. The reaction process was under the central control by HPLC, and when the residual p-toluenesulfonyl chloride was less than 1%, the heat preservation was terminated. After the suction filtration of the reaction solution, the filtrate was washed three times with 100 g of pure water, dried with anhydrous sodium sulfate, filtered, and concentrated, to obtain 80.3 g of Intermediate B with a purity of 96.51%, which was directly used in the next reaction without further purification.

LCMS was used to confirm the structure of Intermediate E. By means of the software accompanied with the instrument, 319 and 320 molecular fragment peaks were obtained in the mass spectrometry analysis. The molecular weight of the product is 318, consistent with T+1 and T+2.

1.1.6 Preparation of Product C1

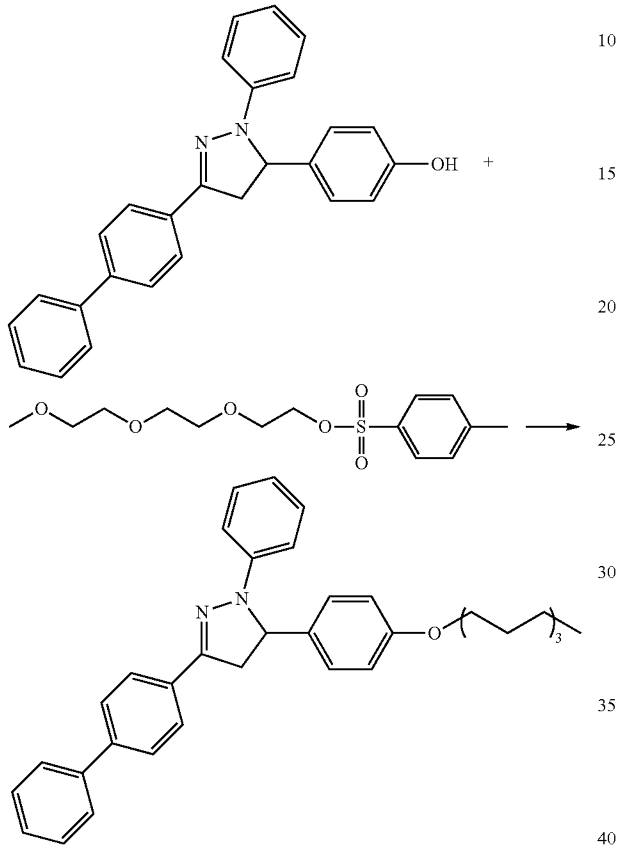

To a four-necked flask 68.0 g of Intermediate E, 250.0 g of acetonitrile, 73.6 g of Intermediate D, and 49.1 g of potassium carbonate were successively added. Under stirring and heating to 80° C., the reaction was conducted under heat preservation. The reaction process was under the central control by HPLC, and when the residual Intermediate D was less than 1%, the heat preservation was terminated. 300 g of pure water and 300 g of ethyl acetate were added, and the aqueous layer was separated. The upper organic layer was washed twice with water, and the ethyl acetate was distilled under reduced pressure to a single-fold amount, and 100 mL of methanol was added. The system was filtered and dried, to obtain 92.2 g of Product C1 with a purity of 99.12%.

LCMS was used to confirm the structure of Product C1. By means of the software accompanied with the instrument, 537 and 538 molecular fragment peaks were obtained in the mass spectrometry analysis. The molecular weight of the product is 536, consistent with T+1 and T+2.

The structure of Product C1 was further confirmed by NMR, and the data are as follows:

$^1$H NMR (400 MHz, DMSO-d6) 7.83 (d, 2H), 7.74 (d, 4H), 7.49 (t, 2H), 7.39 (t, 1H), 7.22 (d, 2H), 7.17 (t, 2H), 7.05 (d, 2H), 6.91 (d, 2H), 6.73 (t, 1H), 5.46 (dd, 1H), 4.06 (t, 2H), 3.71 (t, 2H), 3.57 (d, 2H), 3.56-3.22 (m, 8H), 3.14 (s, 3H) ppm.

1.2 Preparation of Product C2

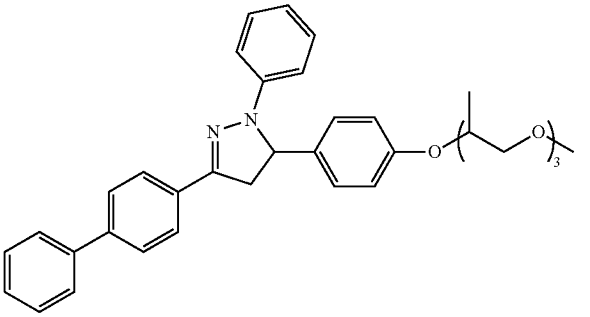

In accordance with the synthesis method for Product C1, the raw material f, namely triethylene glycol monomethyl ether, was replaced with tripropylene glycol monomethyl ether, to obtain Product C2 with a purity of 99.28%.

LCMS was used to confirm the structure of Product C2. By means of the software accompanied with the instrument, 579 and 580 molecular fragment peaks were obtained in the mass spectrometry analysis. The molecular weight of the product is 578, consistent with T+1 and T+2.

The structure of Product C2 was further confirmed by NMR, and the data are as follows:

$^1$H NMR (400 MHz, DMSO-d6) 7.85 (d, 2H), 7.74 (d, 4H), 7.50 (t, 2H), 7.38 (t, 1H), 7.25 (d, 2H), 7.13 (t, 2H), 7.04 (d, 2H), 6.96 (d, 2H), 6.73 (t, 1H), 5.47 (dd, 1H), 4.06 (m, 1H), 3.71 (m, 2H), 3.56-3.22 (m, 17H), 3.19 (s, 3H) ppm.

1.3 Preparation of Product C3

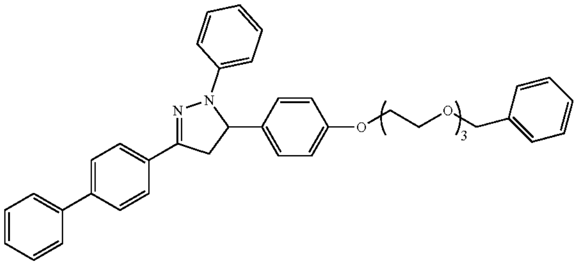

In accordance with the synthesis method for Product C1, the raw material f, namely triethylene glycol monomethyl ether, was replaced with triethylene glycol monobenzyl ether, to obtain Product C3 with a purity of 99.54%.

LCMS was used to confirm the structure of Product C3. By means of the software accompanied with the instrument, 613 and 614 molecular fragment peaks were obtained in the mass spectrometry analysis. The molecular weight of the product is 612, consistent with T+1 and T+2.

The structure of Product C3 was further confirmed by NMR, and the data are as follows:

$^1$H NMR (400 MHz, DMSO-d6)$^1$H NMR (400 MHz, DMSO-d6) 7.84 (d, 2H), 7.77 (d, 4H), 7.63 (d, 2H), 7.45 (t, 2H), 7.39 (t, 3H), 7.25 (d, 2H), 7.15 (t, 2H), 7.02 (d, 2H), 6.95 (d, 2H), 6.72 (t, 1H), 5.48 (dd, 1H), 4.17 (s, 2H), 4.02 (t, 2H), 3.78 (t, 2H), 3.53 (d, 2H), 3.66-3.32 (m, 8H) ppm.

1.4 Preparation of Product C4

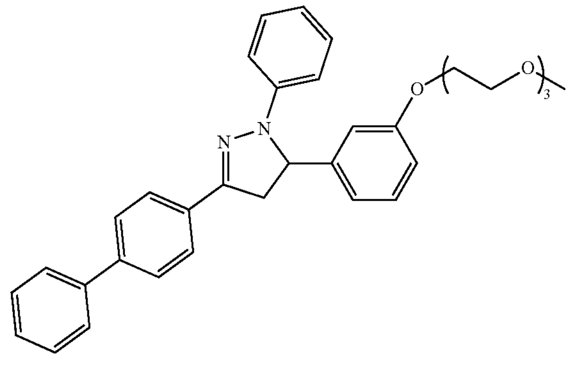

In accordance with the synthesis method for Product C1, the raw material a, namely p-hydroxybenzaldehyde, was replaced with m-hydroxybenzaldehyde, to obtain Product C4 with a purity of 99.17%.

LCMS was used to confirm the structure of Product C4. By means of the software accompanied with the instrument, 537 and 538 molecular fragment peaks were obtained in the mass spectrometry analysis. The molecular weight of the product is 536, consistent with T+1 and T+2.

The structure of Product C4 was further confirmed by NMR, and the data are as follows:

$^{1}H$ NMR (400 MHz, DMSO-d6) 7.89 (d, 2H), 7.78 (d, 2H), 7.70 (s, 1H), 7.61 (t, 2H), 7.54 (t, 2H), 7.35 (t, 1H), 7.29 (d, 2H), 7.21 (t, 2H), 7.14 (d, 2H), 6.98 (d, 2H), 6.80 (t, 1H), 5.52 (dd, 1H), 4.14 (t, 2H), 3.82 (t, 2H), 3.64 (d, 2H), 3.59-3.24 (m, 8H), 3.23 (s, 3H) ppm.

1.5 Preparation of Product C5

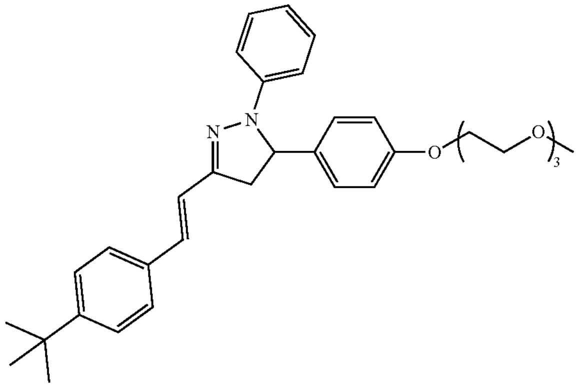

In accordance with the synthesis method for Product C1, the raw material c, namely phenylacetophenone, was replaced with p-tert-butylbenzaldehyde, to obtain Product C5 with a purity of 99.49%.

LCMS was used to confirm the structure of Product C5. By means of the software accompanied with the instrument, 543 and 544 molecular fragment peaks were obtained in the mass spectrometry analysis. The molecular weight of the product is 542, consistent with T+1 and T+2.

The structure of Product C5 was further confirmed by NMR, and the data are as follows:

$^{1}H$ NMR (400 MHz, DMSO-d6) 7.84 (s, 1H), 7.76 (d, 2H), 7.44 (d, 2H), 7.39 (t, 2H), 7.33 (d, 2H), 7.04 (s, 1H), 7.02 (t, 1H), 6.91 (d, 2H), 6.80 (d, 2H), 5.29 (dd, 1H), 4.33 (t, 2H), 3.89 (t, 2H), 3.59-3.42 (m, 10H), 3.40 (s, 3H), 1.36 (s, 9H) ppm.

1.6 Preparation of Product C6

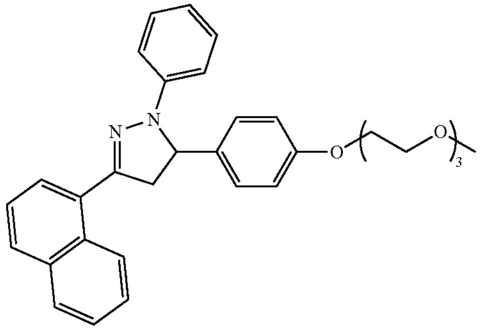

In accordance with the synthesis method for Product C1, the raw material c, namely phenylacetophenone, was replaced with 1-acetonaphthone, to obtain Product C6 with a purity of 99.33%.

LCMS was used to confirm the structure of Product C6. By means of the software accompanied with the instrument, 511 and 512 molecular fragment peaks were obtained in the mass spectrometry analysis. The molecular weight of the product is 510, consistent with T+1 and T+2.

The structure of Product C6 was further confirmed by NMR, and the data are as follows:

$^{1}H$ NMR (400 MHz, DMSO-d6) 8.50 (d, 1H), 8.52 (d, 1H), 7.99 (t, 1H), 7.94 (d, 2H), 7.73 (t, 1H), 7.43 (t, 1H), 7.34-7.21 (m, 4H), 7.13-6.81 (m, 5H), 5.43 (dd, 1H), 4.11 (t, 2H), 3.72 (t, 2H), 3.58 (d, 2H), 3.65-3.25 (m, 8H), 3.17 (s, 3H) ppm.

2. Preparation of Photosensitive Resin Compositions

According to the formulations shown in Table 1, the components were uniformly mixed to prepare the photosensitive resin compositions. Unless otherwise specified, the parts shown in Table 1 are all parts by weight.

TABLE 1

| | Example | | | | | | Comparative Example |
|---|---|---|---|---|---|---|---|
| No. | 1 | 2 | 3 | 4 | 5 | 6 | 1 |
| C1 | 0.2 | | | | | | |
| C2 | | 0.2 | | | | | |
| C3 | | | 0.2 | | | | |
| C4 | | | | 0.2 | | | |
| C5 | | | | | 0.2 | | |
| C6 | | | | | | 0.2 | |
| C7 | | | | | | | 0.2 |
| A1 | 44 | 44 | 44 | 44 | 44 | 44 | 44 |
| A2 | 18 | 18 | 18 | 18 | 18 | 18 | 18 |
| B1 | 14 | 14 | 14 | 14 | 14 | 14 | 14 |
| B2 | 10 | 10 | 10 | 10 | 10 | 10 | 10 |
| B3 | 6 | 6 | 6 | 6 | 6 | 6 | 6 |
| B4 | 5 | 5 | 5 | 5 | 5 | 5 | 5 |
| D | 2 | 2 | 2 | 2 | 2 | 2 | 2 |

TABLE 1-continued

| No. | Example 1 | 2 | 3 | 4 | 5 | 6 | Comparative Example 1 |
|---|---|---|---|---|---|---|---|
| E1 | 0.03 | 0.03 | 0.03 | 0.03 | 0.03 | 0.03 | 0.03 |
| E2 | 0.15 | 0.15 | 0.15 | 0.15 | 0.15 | 0.15 | 0.15 |
| E3 | 0.15 | 0.15 | 0.15 | 0.15 | 0.15 | 0.15 | 0.15 |
| E4 | 0.1 | 0.1 | 0.1 | 0.1 | 0.1 | 0.1 | 0.1 |
| E5 | 0.17 | 0.17 | 0.17 | 0.17 | 0.17 | 0.17 | 0.17 |
| E6 | 30 | 30 | 30 | 30 | 30 | 30 | 30 |
| E7 | 0.2 | 0.2 | 0.2 | 0.2 | 0.2 | 0.2 | 0.2 |

The meanings of the symbols for respective components in Table 1 were as shown in Table 2 below.

TABLE 2

| Ingredient | No. | Specific component |
|---|---|---|
| Alkali-soluble polymer | A1 | Acrylic copolymer, in butanone solution, the copolymer accounting for 30 parts by weight, having a composition of methyl methacrylate/methacrylic acid/n-butyl acrylate (mass ratio 70/20/10), an acid equivalent of 334, and a weight-average molecular weight of 120,000 (CHANGZHOU TRONLY NEW ELECTRONIC MATERIALS CO., LTD.) |
| | A2 | Acrylic copolymer, in butanone solution, the copolymer accounting for 43 parts by weight, having a composition of methyl methacrylate/methacrylic acid/n-butyl acrylate (mass ratio 50/30/20), an acid equivalent of 340, and a weight-average molecular weight of 50,000 (CHANGZHOU TRONLY NEW ELECTRONIC MATERIALS CO., LTD.) |
| Compound having an ethylenically unsaturated double bond | B1 | Urethane compound of hexamethylene diisocyanate and pentapropylene glycol monomethacrylate (Shin-nakamura Chemical Co. Ltd.) |
| | B2 | Dipentaerythritol hexaacrylate (Shin-nakamura Chemical Co. Ltd.) |
| | B3 | Tetra-nonylphenylheptaethylene glycol dipropylene glycol acrylate (Asahi Kasei Co., Ltd.) |
| | B4 | Triacrylate with an average of 3 moles of cyclohexane added to p-trimethylolpropane (Hitachi Chemical Co., Ltd.) |
| Pyrazoline sensitizer | C7 | 1-Phenyl-3-biphenyl-5-(4-tert-butylphenyl)pyrazoline |
| Other photoinitiator and/or sensitizer | D | BCIM (CHANGZHOU TRONLY NEW ELECTRONIC MATERIALS CO., LTD.) |
| Auxiliary agent | E1 | Malachite green (Hangzhou Hairui Chemical Co., Ltd.) |
| | E2 | Leuco Crystal Violet (Hangzhou Hairui Chemical Co., Ltd.) |
| | E3 | 5-Carboxy-1,2,3-benzotriazole (Alpha Chemical Co., Ltd.) |
| | E4 | 2,6-Di-tert-butyl-p-cresol (Hangzhou Hairui Chemical Co., Ltd.) |
| | E5 | N-phenylglycine (Hubei Jusheng Technology Co., Ltd.) |
| | E6 | Acetone |
| | E7 | 2-(4-Ethylbiphenyl)-4,6-bis(trichloromethyl)-1,3,5-triazine (CHANGZHOU TRONLY NEW ELECTRONIC MATERIALS CO., LTD.) |

3 Performance Evaluations

3.1 Evaluation Manners

<Production of Dry Film>

The photosensitive resin composition was thoroughly stirred, uniformly coated on the surface of 25 μm-thick polyethylene glycol terephthalate film as a support using a bar coater, and dried in a dryer at 95° C. for 5 minutes, to form a 40 μm-thick photosensitive resin layer. Then, a 15 μm-thick polyethylene film as a protective layer was adhered on the surface of the photosensitive resin layer on which the polyethylene glycol terephthalate film was not laminated, to obtain a dry film.

<Substrate Surface Leveling>

As the substrate, a 1.2 mm-thick copper clad laminate laminated with a 35 μm-thick rolled copper foil was used, and the surface was subjected to wet polishing roll grinding (Scotch-Brite (registered trademark) HD #600 manufactured by 3M, passed twice).

<Laminating>

The polyethylene film protective layer was peeled off from the dry film, and then laminated on a copper clad laminate preheated to 60° C. at a roll temperature of 105° C. using a hot roll laminator (AL-70 from Asahi Kasei Co., Ltd.). The gas pressure was 0.35 MPa, and the laminating speed was 1.5 m/min.

<Exposure>

The mask was placed on a polyethylene glycol terephthalate film as the support, and the photosensitive layer was exposed using an ultra-high pressure mercury lamp (HMW-201 KB manufactured by ORCMANUFACTURINGCO., LTD.) with an irradiation energy of 60 $mJ/cm^2$.

<Development>

The polyethylene glycol terephthalate film was peeled off. Using an alkali developing device (a developing device for dry film manufactured by FujiKiko Co., Ltd.), a 1 mass % $Na_2CO_3$ aqueous solution at 30° C. was sprayed on the photosensitive resin layer. The unexposed portion of the photosensitive resin layer was dissolved and removed over a period twice as long as the minimum development time. The shortest time required to completely dissolve the photosensitive resin layer in the unexposed portion was the minimum development time.

3.2 Evaluation Contents (1) Compatibility Evaluation

The photosensitive resin composition having the composition shown in Table 1 was thoroughly stirred, mixed, and uniformly coated on the surface of 19 μm-thick polyethylene glycol terephthalate film as a support using a bar coater. It was dried in a dryer at 95° C. for 4 min, to form a photosensitive resin layer. Thereafter, the coated surface was visually inspected and graded as follows:

○: The coated surface was uniform;

•: Undissolved matters were separated out on the coated surface.

(2) Photosensitivity Evaluation

The laminated substrate was exposed for 15 minutes, using a 21-grade stepwise exposure table manufactured by Stouffer with 21-grade brightness changes from transparent to black, to evaluate the photosensitivity thereof. After exposure, it was developed over a period twice as long as the minimum development time, according to the exposure level where the grade in the stepwise exposure table is 8 in case of the completely residual resist film. It was graded as follows:

○: The exposure level was 20 $mJ/cm^2$ or less;

◎: The exposure level was 20 $mJ/cm^2$-50 $mJ/cm^2$ (excluding endpoints);

•: The exposure level was 50 $mJ/cm^2$ or more.

(3) Resolution Evaluation

Through line pattern mask with a width ratio of 1:1 between the exposed and unexposed portions, the laminated substrate was exposed for 15 minutes, and developed over a period twice as long as the minimum development time. The minimum mask line width for normally forming the cured resist line served as the resolution value, and it was graded as follows:

○: The resolution value was 30 μm or less;

◎: The resolution value was 30 μm-50 μm, (excluding endpoints);

•: The resolution value was 50 μm or more.

(4) Developing Property Evaluation

The photosensitive layer (resist layer) having a thickness of 40 μm and an area of 0.16 $m^2$ in the photosensitive resin laminate was dissolved in 200 ml of 1 mass % $Na_2CO_3$ aqueous solution, which was sprayed for 3 hours under a spraying pressure of 0.1 MPa using a circulating sprayer. Then, the developer was left to stand for 1 day, to observe the appearance of aggregates. If the aggregates were appeared in large quantities, powdery or oily substances may be observed on the bottom or sides of the sprayer. In addition, sometimes the aggregates may be floated in the developer. For the composition with good developer aggregation property, these aggregates do not appear at all, or even if they appear, they can be easily washed out from the sprayer by washing with a very small amount of water. By visual observation of the appearance of aggregates, it was graded as follows:

○: There were no aggregates on the bottom or sides of the sprayer, and a very small amount of aggregates being floated in the developer that can be visually confirmed can be observed, but can be easily washed off when washed with water;

◎: There were aggregates on part of the bottom or sides of the sprayer and floated in the developer, which cannot be completely washed off even if being washed with water;

•: The aggregates were visible in the entire sprayer and floated in the developer, which cannot be completely washed off and most of which were remained, even if being washed with water.

(5) Adhesion Evaluation

Through line pattern mask with a width ratio of 1:100 between the exposed and unexposed portions, the laminated substrate was exposed for 15 minutes, and developed over a development period twice as long as the minimum development time. The minimum mask line width for normally forming the cured resist line served as the adhesion value.

○: The adhesion value was 30 μm or less;

◎: The adhesion value was 30 μm-50 μm, (excluding endpoints);

●: The adhesion value was 50 μm or more.

3.3 Evaluation Results

The evaluation results are shown in Table 3.

TABLE 3

| | Compatibility | Photo-sensitivity | Resolution | Developing property | Adhesion |
|---|---|---|---|---|---|
| Example 1 | ○ | 15/○ | 25/○ | ○ | 25/○ |
| Example 2 | ○ | 16/○ | 26/○ | ○ | 28/○ |
| Example 3 | ○ | 16/○ | 28/○ | ○ | 26/○ |
| Example 4 | ○ | 15/○ | 27/○ | ○ | 26/○ |
| Example 5 | ○ | 18/○ | 28/○ | ○ | 28/○ |
| Example 6 | ○ | 18/○ | 27/○ | ○ | 27/○ |
| Comparative Example 1 | ● | 31/◎ | 42/◎ | ● | 40/◎ |

When the EO/PO modified pyrazoline sensitizer of the invention is applied in the photosensitive resin composition, the product has high compatibility, high photosensitivity, high resolution, high solubility, high adhesion, and excellent developing property, as well as better hydrophilicity during development, and can significantly reduce the amount of sludges in the recycled developer, so that the developer can be repeated for many times and effectively used. The photosensitive resin composition can be widely applied in the manufacture of printed circuit boards, protective patterns, conductor patterns, lead frames, semiconductor packages, and the like in a manner of dry and wet films.

The above descriptions are merely preferred embodiments of the invention and are not intended to limit the invention. For those skilled in the art, the invention may have various modifications and changes. Any modification, equivalent replacement, and improvement made within the spirit and principle of the invention shall be included within the scope of the invention.

What is claimed is:

1. An ethoxy/propoxy modified pyrazoline organic compound, wherein the ethoxy/propoxy modified pyrazoline organic compound has a structure represented by Formula (I):

Formula (I)

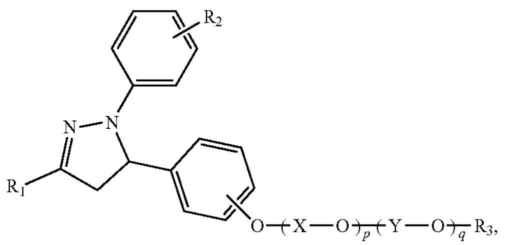

wherein X and Y each independently represent $—CH_2—CH_2—$ or $—CH(CH_3)—CH_2—$;

p and q each independently represent an integer from 0 to 9, and both are not 0 at the same time;

$R_1$ represents a substituent group having a conjugated structure with the pyrazole ring;

$R_2$ represents hydrogen, $C_1$ to $C_{10}$ linear or branched alkyl, or $C_4$ to $C_{10}$ alkylcycloalkyl or cycloalkylalkyl;

$R_3$ represents hydrogen, $C_1$ to $C_{20}$ hydrocarbon group, or $C_6$ to $C_{20}$ arylalkyl, provided that when $R_2$ is hydrogen, $R_1$ is not phenyl.

2. The ethoxy/propoxy modified pyrazoline organic compound according to claim 1, wherein p+q≤9.

3. The ethoxy/propoxy modified pyrazoline organic compound according to claim 1, wherein $R_1$ is selected from phenyl, naphthyl, pyrrolyl, imidazolyl, carbazolyl, indolyl, $C_2$ to $C_{10}$ alkenyl, or $C_4$ to $C_8$ cyclodienyl, or the hydrogen atom(s) therein may be each independently substituted by: $C_1$ to $C_{10}$ linear or branched alkyl, $C_4$ to $C_{10}$ alkylcycloalkyl or cycloalkylalkyl, $C_3$ to $C_{10}$ cycloalkyl, $C_6$ to $C_{15}$ aryl, $C_6$ to $C_{12}$ alkylaryl, $C_6$ to $C_{12}$ arylalkyl, or $C_2$ to $C_{20}$ heteroaryl;

$R_2$ is selected from hydrogen, or $C_1$ to $C_6$ linear or branched alkyl;

$R_3$ is selected from hydrogen, $C_1$ to $C_6$ linear or branched alkyl, or benzyl.

4. The ethoxy/propoxy modified pyrazoline organic compound according to claim 3, wherein $R_1$ is selected from phenyl, naphthyl, pyrrolyl, imidazolyl, carbazolyl, indolyl, $C_2$ to $C_6$ alkenyl, $C_4$ to $C_6$ cyclodienyl, phenyl substituted by $C_1$ to $C_5$ alkyl, phenyl substituted by $C_3$ to $C_6$ cycloalkyl, alkenyl substituted by $C_6$ to $C_{10}$ aryl, alkenyl substituted by $C_6$ to $C_{10}$ alkylaryl, or alkenyl substituted by $C_6$ to $C_{10}$ arylalkyl.

5. The ethoxy/propoxy modified pyrazoline organic compound according to claim 4, wherein $R_1$ is selected from:

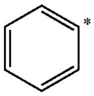,
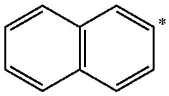,
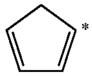,
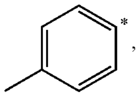,

-continued

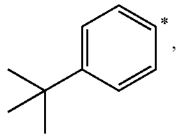,
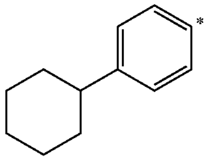,
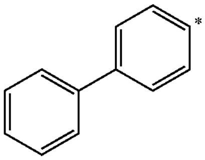,
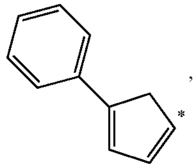,
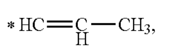,
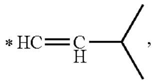,
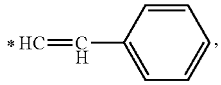,
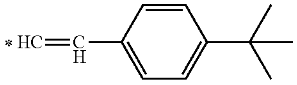
or.
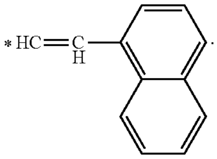.

6. The ethoxy/propoxy modified pyrazoline organic compound according to claim 2, wherein $R_2$ is selected from hydrogen, methyl, ethyl, propyl, isopropyl, butyl, tert-butyl, or $CH_3C(CH_2CH_3)_2$—.

7. The ethoxy/propoxy modified pyrazoline organic compound according to claim 6, wherein the ethoxy/propoxy modified pyrazoline organic compound is selected from the group consisting of the following organic compounds:

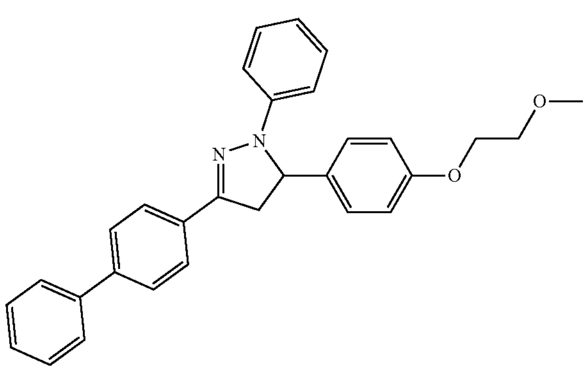

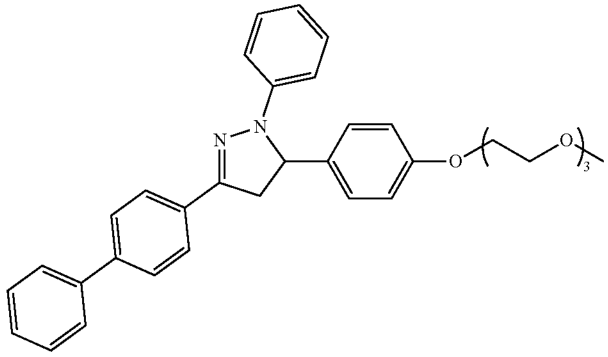

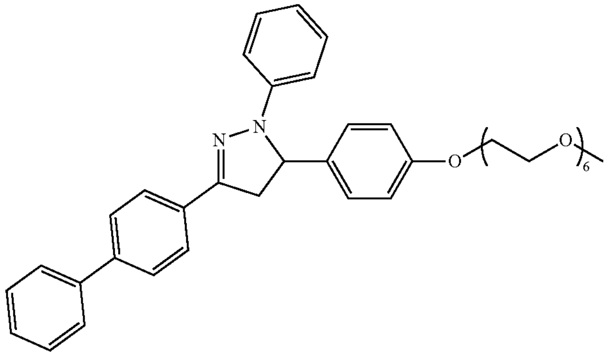

-continued
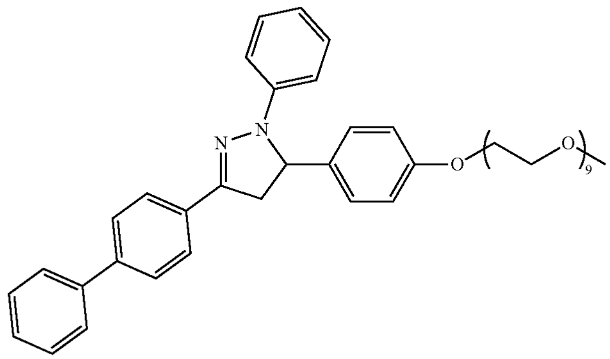
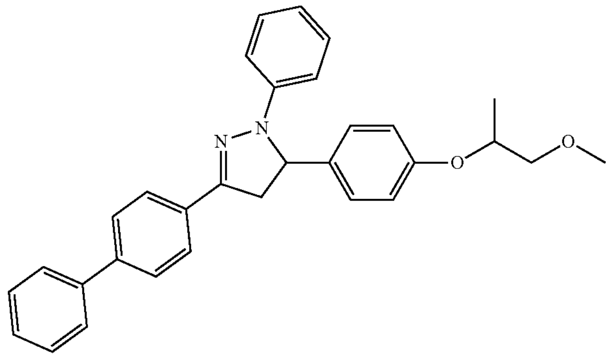
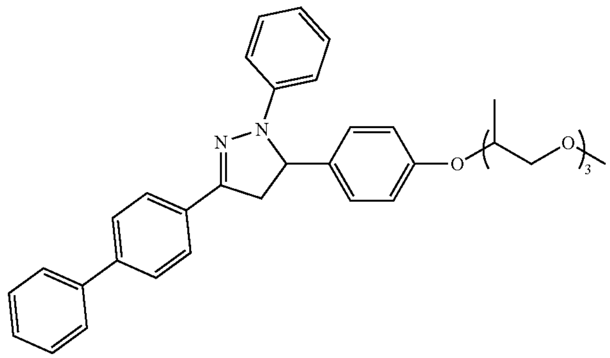
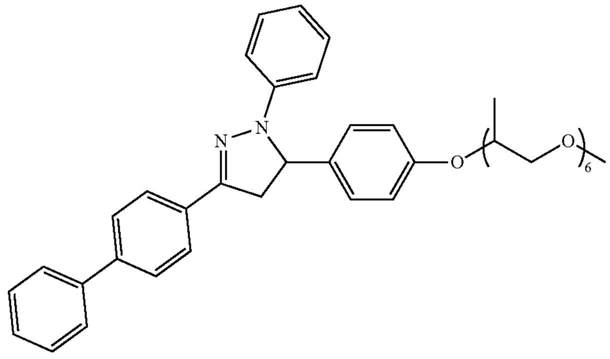

-continued
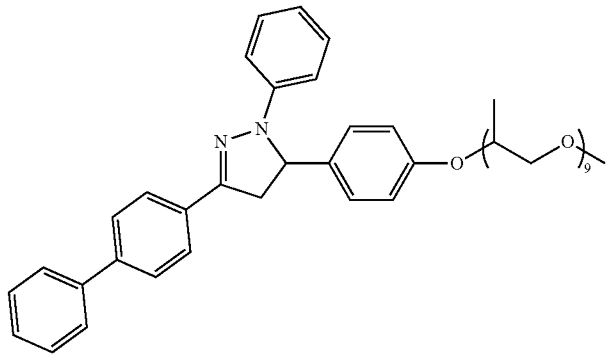
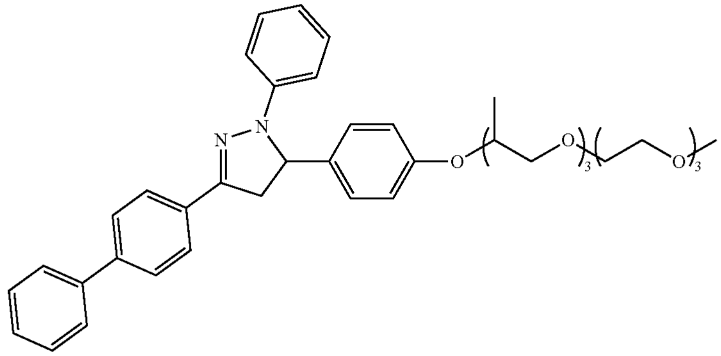
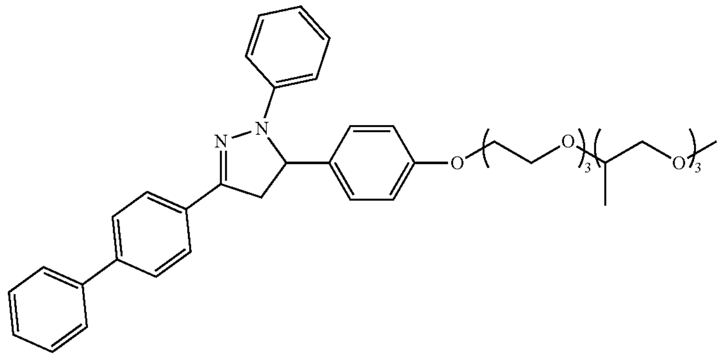
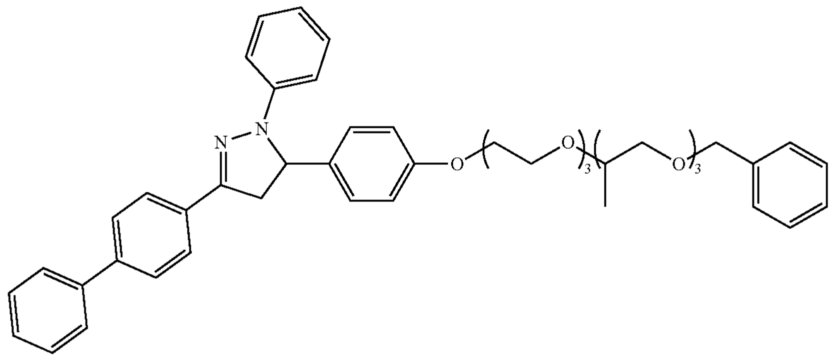

-continued
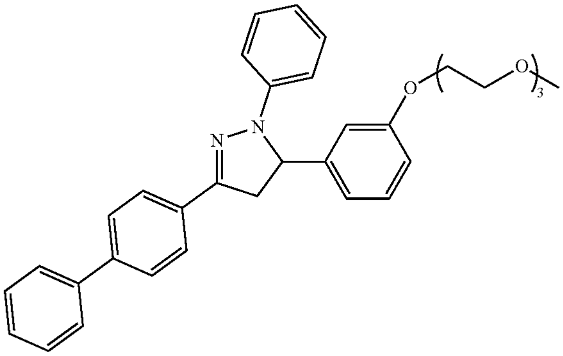
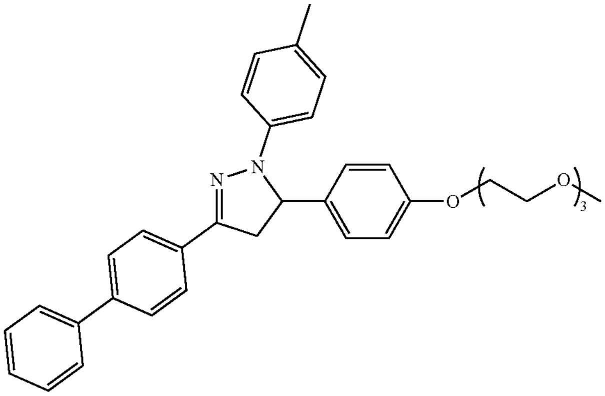
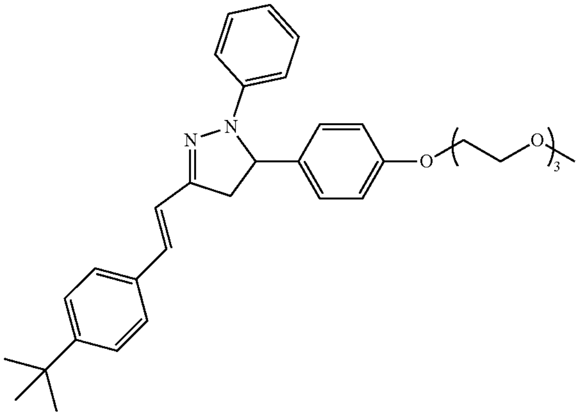
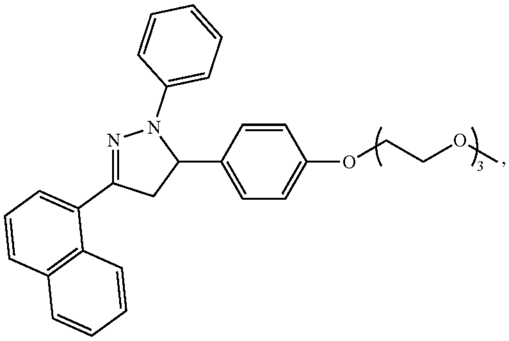
,

-continued

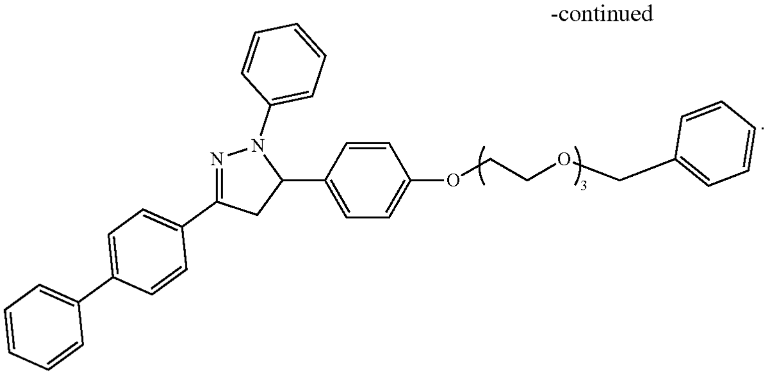

8. A photocurable composition, comprising: (A) an alkali-soluble polymer, (B) a compound having an ethylenically unsaturated double bond, (C) a first sensitizer, (D) a photoinitiator and/or a second sensitizer, and (E) other optional auxiliary agent(s), wherein the first sensitizer is the ethoxy/propoxy modified pyrazoline organic compound according to claim 1, and the second sensitizer is of a different kind from the first sensitizer.

9. The photocurable composition according to claim 8, wherein the alkali-soluble polymer is selected from one or more of the group consisting of (meth)acrylic polymers, styrenic polymers, epoxy polymers, aliphatic polyurethane (meth)acrylate polymers, aromatic polyurethane (meth) acrylate polymers, amide resins, amide epoxy resins, alkyd resins, and phenolic resins.

10. The photocurable composition according to claim 9, wherein the compound having an ethylenically unsaturated double bond is selected from one or more of the group consisting of compounds obtained by reacting α,β-unsaturated carboxylic acids with polyols, bisphenol A-based (meth)acrylate compounds, compounds obtained by reacting α,β-unsaturated carboxylic acids with glycidyl-containing compounds, (meth)acrylate compounds having a urethane bond in the molecule, nonylphenoxypolyethyleneoxyacrylates, γ-chloro-β-hydroxypropyl-β'-(meth)acryloyloxyethyl-phthalates, β-hydroxyethyl-β'-(meth)acryloyloxyethyl-phthalates, β-hydroxypropyl-β'-(meth)acryloyloxyethyl-phthalates, benzene dicarboxylic acid compounds, and alkyl (meth)acrylates.

11. The photocurable composition according to claim 9, wherein the auxiliary agent is selected from one or more of the group consisting of hydrogen donors, dyes, pigments, light chromogenic reagents, fillers, plasticizers, stabilizers, coating aids, and stripping promoters.

12. The ethoxy/propoxy modified pyrazoline organic compound according to claim 1, wherein $p+q \leq 6$.

* * * * *